US012799206B2

(12) United States Patent
Liu et al.

(10) Patent No.: US 12,799,206 B2
(45) Date of Patent: Nov. 17, 2026

(54) ANTI-SIGLEC COMPOSITIONS AND USES THEREOF

(71) Applicants: ONCOC4, INC., Rockville, MD (US); UNIVERSITY OF MARYLAND, BALTIMORE, Baltimore, MD (US)

(72) Inventors: Yang Liu, Potomac, MD (US); Pan Zheng, Potomac, MD (US); Martin Devenport, Gaithersburg, MD (US); Mingyue Liu, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 448 days.

(21) Appl. No.: 18/558,112

(22) PCT Filed: Apr. 29, 2022

(86) PCT No.: PCT/US2022/027006
§ 371 (c)(1),
(2) Date: Oct. 30, 2023

(87) PCT Pub. No.: WO2022/232558
PCT Pub. Date: Nov. 3, 2022

(65) Prior Publication Data

US 2024/0218067 A1 Jul. 4, 2024

Related U.S. Application Data

(60) Provisional application No. 63/182,271, filed on Apr. 30, 2021.

(51) Int. Cl.

| | |
|---|---|
| ***C07K 16/28*** | (2006.01) |
| ***A61K 39/395*** | (2006.01) |
| ***A61P 35/00*** | (2006.01) |
| *A61K 39/00* | (2006.01) |

(52) U.S. Cl.
CPC .......... *C07K 16/2818* (2013.01); *A61P 35/00* (2018.01); *A61K 39/395* (2013.01); *A61K 2039/507* (2013.01); *C07K 2317/24* (2013.01); *C07K 2317/565* (2013.01)

(58) Field of Classification Search
CPC ............ C07K 16/2803; C07K 16/2818; C07K 2317/24; C07K 2317/565; C07K 2317/73; C07K 2317/732; C07K 2317/76; C07K 2317/92; A61P 35/00; A61K 2039/505; A61K 2039/507; A61K 2039/545
See application file for complete search history.

(56) References Cited

U.S. PATENT DOCUMENTS

2012/0171114 A1 7/2012 Haeuw
2012/0201819 A1 8/2012 Liu
2018/0344829 A1 12/2018 Pharma

FOREIGN PATENT DOCUMENTS

WO 2015107171 A1 7/2015
WO 2020198353 A1 10/2020

OTHER PUBLICATIONS

Almagro et al., Frontiers in Immunology, 2018, 8: 1751, pp. 1-19.*
Herold et al. (Science Reports, 2017, 7(1):12276, pp. 1-17.*
Murphy et al., Journal of Immunological Methods, 2018, 463: 127-133.*
Duan, Shiteng, et al., "Siglecs as Immune Cell Checkpoints in Disease," Annual Review of Immunology, Jan. 27, 2020, 31 pages.
Supplementary European Search Report for EP Application No. 22796839.3, dated Sep. 9, 2025, 10 pages.
Search Report for Taiwanese Patent Application No. 111116333, dated Sep. 26, 2025, 7 pages.

* cited by examiner

*Primary Examiner* — Hong Sang
(74) *Attorney, Agent, or Firm* — Ron Galant; Polsinelli PC

(57) ABSTRACT

The disclosure relates to anti-Siglec-10 antibodies and the use of such antibodies in cancer therapy.

28 Claims, 26 Drawing Sheets

Specification includes a Sequence Listing.

SEQUENCE LISTING

```
<160> NUMBER OF SEQ ID NOS: 35

<210> SEQ ID NO 1
<211> LENGTH: 120
<212> TYPE: PRT
<213> ORGANISM: Mus musculus

<400> SEQUENCE: 1

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30
```

```
Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Val Arg Gly Leu Tyr Gly Asn Trp Phe Phe Asp Val Trp Gly Ala
            100                 105                 110

Gly Thr Thr Val Thr Val Ser Ser
        115                 120


<210> SEQ ID NO 2
<211> LENGTH: 107
<212> TYPE: PRT
<213> ORGANISM: Mus musculus

<400> SEQUENCE: 2

Asp Ile Val Met Thr Gln Ser Gln Lys Phe Met Ser Thr Ser Val Gly
1               5                   10                  15

Asp Arg Val Ser Ile Thr Tyr Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asn Leu Ala Asn Tyr Phe Cys Gln Gln Tyr Ser Ser Tyr Pro Leu
                85                  90                  95

Thr Phe Gly Ala Gly Thr Lys Leu Glu Leu Lys
            100                 105


<210> SEQ ID NO 3
<211> LENGTH: 7
<212> TYPE: PRT
<213> ORGANISM: Mus musculus

<400> SEQUENCE: 3

Thr Ser Gly Met Gly Leu Ser
1               5


<210> SEQ ID NO 4
<211> LENGTH: 16
<212> TYPE: PRT
<213> ORGANISM: Mus musculus

<400> SEQUENCE: 4

His Ile Tyr Trp Asp Asp Asp Lys Arg Tyr Asn Pro Ser Leu Lys Ser
1               5                   10                  15


<210> SEQ ID NO 5
<211> LENGTH: 10
<212> TYPE: PRT
<213> ORGANISM: Mus musculus

<400> SEQUENCE: 5

Gly Leu Tyr Gly Asn Trp Phe Phe Asp Val
1               5                   10
```

<210> SEQ ID NO 6
<211> LENGTH: 11
<212> TYPE: PRT
<213> ORGANISM: Mus musculus

<400> SEQUENCE: 6

```
Lys Ala Ser Gln Asn Val Gly Thr Ala Val Ala
1               5                   10
```

<210> SEQ ID NO 7
<211> LENGTH: 7
<212> TYPE: PRT
<213> ORGANISM: Mus musculus

<400> SEQUENCE: 7

```
Ser Ala Ser Asn Arg Tyr Thr
1               5
```

<210> SEQ ID NO 8
<211> LENGTH: 10
<212> TYPE: PRT
<213> ORGANISM: Mus musculus

<400> SEQUENCE: 8

```
Gln Gln Tyr Ser Ser Tyr Pro Leu Thr Phe
1               5                   10
```

<210> SEQ ID NO 9
<211> LENGTH: 120
<212> TYPE: PRT
<213> ORGANISM: Artificial
<220> FEATURE:
<223> OTHER INFORMATION: Humanizied antibody

<400> SEQUENCE: 9

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Gly Leu Tyr Gly Asn Trp Phe Phe Asp Val Trp Gly Gln
            100                 105                 110

Gly Thr Thr Val Thr Val Ser Ser
        115                 120
```

<210> SEQ ID NO 10
<211> LENGTH: 120
<212> TYPE: PRT
<213> ORGANISM: Artificial
<220> FEATURE:
<223> OTHER INFORMATION: humanized antibody

<400> SEQUENCE: 10

```
Gln Val Thr Leu Lys Glu Ser Gly Pro Ala Leu Val Lys Pro Thr Gln
```

1 5 10 15

Thr Leu Thr Leu Thr Cys Thr Phe Ser Gly Phe Ser Leu Ser Thr Ser
20 25 30

Gly Met Gly Leu Ser Trp Ile Arg Gln Pro Pro Gly Lys Ala Leu Glu
35 40 45

Trp Leu Ala His Ile Tyr Trp Asp Asp Asp Lys Arg Tyr Asn Pro Ser
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Val Arg Gly Leu Tyr Gly Asn Trp Phe Phe Asp Val Trp Gly Ala
100 105 110

Gly Thr Thr Val Thr Val Ser Ser
115 120

<210> SEQ ID NO 11
<211> LENGTH: 120
<212> TYPE: PRT
<213> ORGANISM: Artificial
<220> FEATURE:
<223> OTHER INFORMATION: humanized antibody

<400> SEQUENCE: 11

Gln Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Gly Met Gly Leu Ser Trp Ile Arg Gln Pro Pro Gly Lys Ala Leu Glu
35 40 45

Trp Leu Ala His Ile Tyr Trp Asp Asp Asp Lys Arg Tyr Asn Pro Ser
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Gly Leu Tyr Gly Asn Trp Phe Phe Asp Val Trp Gly Gln
100 105 110

Gly Thr Thr Val Thr Val Ser Ser
115 120

<210> SEQ ID NO 12
<211> LENGTH: 120
<212> TYPE: PRT
<213> ORGANISM: Artificial
<220> FEATURE:
<223> OTHER INFORMATION: humanized antibody

<400> SEQUENCE: 12

Gln Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Gly Met Gly Leu Ser Trp Ile Arg Gln Pro Pro Gly Lys Ala Leu Glu
35 40 45

Trp Leu Ala His Ile Tyr Trp Asp Asp Asp Lys Arg Tyr Asn Pro Ser
50 55 60

```
Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Leu Tyr Gly Asn Trp Phe Phe Asp Val Trp Gly Ala
            100                 105                 110

Gly Thr Thr Val Thr Val Ser Ser
        115                 120


<210> SEQ ID NO 13
<211> LENGTH: 120
<212> TYPE: PRT
<213> ORGANISM: Artificial
<220> FEATURE:
<223> OTHER INFORMATION: humanized antibody

<400> SEQUENCE: 13

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Leu Tyr Gly Asn Trp Phe Phe Asp Val Trp Gly Gln
            100                 105                 110

Gly Thr Leu Val Thr Val Ser Ser
        115                 120


<210> SEQ ID NO 14
<211> LENGTH: 107
<212> TYPE: PRT
<213> ORGANISM: Artificial
<220> FEATURE:
<223> OTHER INFORMATION: humanized antibody

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu
                85                  90                  95

Thr Phe Gly Gly Gly Thr Lys Val Glu Ile Lys
            100                 105


<210> SEQ ID NO 15
```

<211> LENGTH: 107
<212> TYPE: PRT
<213> ORGANISM: Artificial
<220> FEATURE:
<223> OTHER INFORMATION: humanized antibody

<400> SEQUENCE: 15

```
Asp Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Leu
                85                  90                  95

Thr Phe Gly Gly Gly Thr Lys Val Glu Ile Lys
            100                 105
```

<210> SEQ ID NO 16
<211> LENGTH: 107
<212> TYPE: PRT
<213> ORGANISM: Artificial
<220> FEATURE:
<223> OTHER INFORMATION: humanized antibody

<400> SEQUENCE: 16

```
Glu Ile Val Met Thr Gln Ser Pro Ala Thr Leu Ser Val Ser Pro Gly
1               5                   10                  15

Glu Arg Ala Thr Leu Ser Tyr Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu
                85                  90                  95

Thr Phe Gly Gly Gly Thr Lys Val Glu Ile Lys
            100                 105
```

<210> SEQ ID NO 17
<211> LENGTH: 107
<212> TYPE: PRT
<213> ORGANISM: Artificial
<220> FEATURE:
<223> OTHER INFORMATION: humanized antibody

<400> SEQUENCE: 17

```
Asp Ile Val Met Thr Gln Ser Pro Ala Thr Leu Ser Val Ser Pro Gly
1               5                   10                  15

Glu Arg Ala Thr Leu Ser Tyr Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45
```

```
Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Leu
                85                  90                  95

Thr Phe Gly Gly Gly Thr Lys Val Glu Ile Lys
            100                 105


<210> SEQ ID NO 18
<211> LENGTH: 107
<212> TYPE: PRT
<213> ORGANISM: Artificial
<220> FEATURE:
<223> OTHER INFORMATION: humanized antibody

<400> SEQUENCE: 18

Asp Ile Val Met Thr Gln Ser Pro Ala Thr Leu Ser Val Ser Pro Gly
1               5                   10                  15

Glu Arg Ala Thr Leu Thr Tyr Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Leu
                85                  90                  95

Thr Phe Gly Gly Gly Thr Lys Val Glu Ile Lys
            100                 105


<210> SEQ ID NO 19
<211> LENGTH: 106
<212> TYPE: PRT
<213> ORGANISM: Homo sapiens

<400> SEQUENCE: 19

Arg Thr Val Ala Ala Pro Ser Val Phe Ile Phe Pro Pro Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 20
<211> LENGTH: 326
<212> TYPE: PRT
<213> ORGANISM: Homo sapiens

<400> SEQUENCE: 20
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 21
<211> LENGTH: 125
<212> TYPE: PRT
<213> ORGANISM: Artificial
<220> FEATURE:
<223> OTHER INFORMATION: Humanized antibody

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30
```

-continued

```
Gly Leu Ser Trp Ile Arg Gln Pro Pro Gly Lys Gly Leu Glu Trp Ile
        35                  40                  45

Gly Tyr Ile Trp Tyr Asp Gly Asn Thr Asn Phe His Ser Pro Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Thr Glu Gly His Tyr Tyr Gly Ser Asn Tyr Gly Tyr Tyr Ala Leu
            100                 105                 110

Asp Tyr Trp Gly Gln Gly Thr Leu Val Thr Val Ser Ser
        115                 120                 125


<210> SEQ ID NO 22
<211> LENGTH: 107
<212> TYPE: PRT
<213> ORGANISM: Artificial
<220> FEATURE:
<223> OTHER INFORMATION: Humanized antibody

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Gln Gly Lys Ala Pro Lys Leu Leu Leu
        35                  40                  45

Tyr Ala Ala Thr Asn Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Leu Trp Gly Thr Pro Tyr
                85                  90                  95

Thr Phe Gly Gln Gly Thr Lys Leu Glu Ile Lys
            100                 105


<210> SEQ ID NO 23
<211> LENGTH: 120
<212> TYPE: PRT
<213> ORGANISM: Artificial
<220> FEATURE:
<223> OTHER INFORMATION: Humanized

<400> SEQUENCE: 23

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Gly Leu Tyr Gly Asn Trp Phe Phe Asp Val Trp Gly Gln
```

```
            100                 105                 110

Gly Thr Thr Val Thr Val Ser Ser
        115                 120


<210> SEQ ID NO 24
<211> LENGTH: 327
<212> TYPE: PRT
<213> ORGANISM: Artificial
<220> FEATURE:
<223> OTHER INFORMATION: Mutant human IgG4 Fc

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 25
<211> LENGTH: 447
<212> TYPE: PRT
<213> ORGANISM: Artificial
<220> FEATURE:
<223> OTHER INFORMATION: Humanized antibody

<400> SEQUENCE: 25

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Gly Leu Tyr Gly Asn Trp Phe Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 26
<211> LENGTH: 466
<212> TYPE: PRT
<213> ORGANISM: Artificial
<220> FEATURE:
<223> OTHER INFORMATION: Humanized antibody

<400> SEQUENCE: 26

Met Gly Trp Ser Cys Ile Ile Leu Phe Leu Val Ala Thr Ala Thr Gly
1               5                   10                  15

Val His Ser Gln Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Gly Leu Ser Trp Ile Arg Gln Pro Pro Gly Lys
    50                  55                  60

Ala Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Val Arg Gly Leu Tyr Gly Asn Trp Phe Phe Asp Val
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
```

290 295 300

Asn Ala Lys Thr Lys Pro Arg Glu Glu Gln Phe Asn Ser Thr Tyr Arg
305 310 315 320

Val Val Ser Val Leu Thr Val Leu His Gln Asp Trp Leu Asn Gly Lys
325 330 335

Glu Tyr Lys Cys Lys Val Ser Asn Lys Gly Leu Pro Ser Ser Ile Glu
340 345 350

Lys Thr Ile Ser Lys Ala Lys Gly Gln Pro Arg Glu Pro Gln Val Tyr
355 360 365

Thr Leu Pro Pro Ser Gln Glu Glu Met Thr Lys Asn Gln Val Ser Leu
370 375 380

Thr Cys Leu Val Lys Gly Phe Tyr Pro Ser Asp Ile Ala Val Glu Trp
385 390 395 400

Glu Ser Asn Gly Gln Pro Glu Asn Asn Tyr Lys Thr Thr Pro Pro Val
405 410 415

Leu Asp Ser Asp Gly Ser Phe Phe Leu Tyr Ser Arg Leu Thr Val Asp
420 425 430

Lys Ser Arg Trp Gln Glu Gly Asn Val Phe Ser Cys Ser Val Met His
435 440 445

Glu Ala Leu His Asn His Tyr Thr Gln Lys Ser Leu Ser Leu Ser Leu
450 455 460

Gly Lys
465

<210> SEQ ID NO 27
<211> LENGTH: 214
<212> TYPE: PRT
<213> ORGANISM: Artificial
<220> FEATURE:
<223> OTHER INFORMATION: Humanized antibody

<400> SEQUENCE: 27

Asp Ile Val Met Thr Gln Ser Pro Ala Thr Leu Ser Val Ser Pro Gly
1 5 10 15

Glu Arg Ala Thr Leu Ser Cys Lys Ala Ser Gln Asn Val Gly Thr Ala
20 25 30

Val Ala Trp Tyr Gln Gln Lys Pro Gly Gln Ala Pro Arg Leu Leu Ile
35 40 45

Tyr Ser Ala Ser Asn Arg Tyr Thr Gly Val Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Phe Cys Gln Gln Tyr Ser Ser Tyr Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr

```
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 234
<212> TYPE: PRT
<213> ORGANISM: Artificial
<220> FEATURE:
<223> OTHER INFORMATION: Humanized antibody

<400> SEQUENCE: 28

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ala Thr Leu Ser
            20                  25                  30

Val Ser Pro Gly Glu Arg Ala Thr Leu Ser Cys Lys Ala Ser Gln Asn
        35                  40                  45

Val Gly Thr Ala Val Ala Trp Tyr Gln Gln Lys Pro Gly Gln Ala Pro
    50                  55                  60

Arg Leu Leu Ile Tyr Ser Ala Ser Asn Arg Tyr Thr Gly Val Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Phe Cys Gln Gln Tyr Ser
            100                 105                 110

Ser Tyr Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 29
<211> LENGTH: 107
<212> TYPE: PRT
<213> ORGANISM: Artificial
<220> FEATURE:
<223> OTHER INFORMATION: Synthetic

<400> SEQUENCE: 29

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 30
<211> LENGTH: 329
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 31
<211> LENGTH: 329
<212> TYPE: PRT
<213> ORGANISM: Artificial
<220> FEATURE:
<223> OTHER INFORMATION: Mutant variant

<400> SEQUENCE: 31

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Tyr Ile Thr Arg Glu Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ala Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Ala Ala Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 32
<211> LENGTH: 447
<212> TYPE: PRT
<213> ORGANISM: Artificial
<220> FEATURE:
<223> OTHER INFORMATION: Humanized antibody

<400> SEQUENCE: 32

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Gly Leu Tyr Gly Asn Trp Phe Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 33
<211> LENGTH: 466
<212> TYPE: PRT
<213> ORGANISM: Artificial
<220> FEATURE:
<223> OTHER INFORMATION: Humanized antibody

<400> SEQUENCE: 33

Met Gly Trp Ser Cys Ile Ile Leu Phe Leu Val Ala Thr Ala Thr Gly
1 5 10 15

Val His Ser Gln Val Thr Leu Lys Glu Ser Gly Pro Ala Leu Val Lys
20 25 30

Pro Thr Gln Thr Leu Thr Leu Thr Cys Thr Phe Ser Gly Phe Ser Leu
35 40 45

Ser Thr Ser Gly Met Gly Leu Ser Trp Ile Arg Gln Pro Pro Gly Lys
50 55 60

Ala Leu Glu Trp Leu Ala His Ile Tyr Trp Asp Asp Asp Lys Arg Tyr
65 70 75 80

Asn Pro Ser Leu Lys Ser Arg Leu Thr Ile Ser Lys Asp Thr Ser Lys
85 90 95

Asn Gln Val Val Leu Thr Met Thr Asn Met Asp Pro Val Asp Thr Ala
100 105 110

Thr Tyr Tyr Cys Val Arg Gly Leu Tyr Gly Asn Trp Phe Phe Asp Val
115 120 125

Trp Gly Ala Gly Thr Thr Val Thr Val Ser Ser Ala Ser Thr Lys Gly
130 135 140

Pro Ser Val Phe Pro Leu Ala Pro Cys Ser Arg Ser Thr Ser Glu Ser
145 150 155 160

Thr Ala Ala Leu Gly Cys Leu Val Lys Asp Tyr Phe Pro Glu Pro Val
165 170 175

Thr Val Ser Trp Asn Ser Gly Ala Leu Thr Ser Gly Val His Thr Phe
180 185 190

Pro Ala Val Leu Gln Ser Ser Gly Leu Tyr Ser Leu Ser Ser Val Val
195 200 205

Thr Val Pro Ser Ser Ser Leu Gly Thr Lys Thr Tyr Thr Cys Asn Val
210 215 220

Asp His Lys Pro Ser Asn Thr Lys Val Asp Lys Arg Val Glu Ser Lys
225 230 235 240

Tyr Gly Pro Pro Cys Pro Pro Cys Pro Ala Pro Glu Phe Leu Gly Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser Gln Glu
275 280 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 34
<211> LENGTH: 214
<212> TYPE: PRT
<213> ORGANISM: Artificial
<220> FEATURE:
<223> OTHER INFORMATION: Humanized antibody

<400> SEQUENCE: 34

Glu Ile Val Met Thr Gln Ser Pro Ala Thr Leu Ser Val Ser Pro Gly
1               5                   10                  15

Glu Arg Ala Thr Leu Ser Tyr Lys Ala Ser Gln Asn Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 35
<211> LENGTH: 234
<212> TYPE: PRT
<213> ORGANISM: Artificial
<220> FEATURE:
<223> OTHER INFORMATION: Humanized antibody

<400> SEQUENCE: 35

Met Glu Thr Asp Thr Leu Leu Leu Trp Val Leu Leu Leu Trp Val Pro
1               5                   10                  15

Gly Ser Thr Gly Glu Ile Val Met Thr Gln Ser Pro Ala Thr Leu Ser
            20                  25                  30

Val Ser Pro Gly Glu Arg Ala Thr Leu Ser Tyr Lys Ala Ser Gln Asn
        35                  40                  45

Val Gly Thr Ala Val Ala Trp Tyr Gln Gln Lys Pro Gly Gln Ala Pro
    50                  55                  60

Arg Leu Leu Ile Tyr Ser Ala Ser Asn Arg Tyr Thr Gly Val Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Ser
            100                 105                 110

Ser Tyr Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

ANTI-SIGLEC COMPOSITIONS AND USES THEREOF

FIELD OF THE INVENTION

The present invention relates to anti-Siglec-10 antibodies that selectively bind human Siglec-10, and the use of such antibodies in cancer therapy.

INCORPORATION BY REFERENCE OF SEQUENCE LISTING

The international application as filed included a Sequence Listing in .txt format pursuant to WIPO Standard ST.25 and PCT Rule 5.2. The Sequence Listing, filed on Apr. 29, 2022 with International Application No. PCT/US2022/027006 as file "111005_0900_01PCoo_SequenceListing.txt," created Apr. 20, 2022, having a size of 53,500 bytes, formed part of the international application as filed and is part of the present national stage application. The contents of that Sequence Listing are incorporated herein by reference in their entirety.

BACKGROUND OF THE INVENTION

CD24 is a small heavily glycosylated mucin-like glycosylphosphatidyl-inositol (GPI) linked cell surface protein. CD24 is expressed at higher level on hematopoietic cells, including B cells, T cells, neutrophils, eosinophils, dendritic cells, and macrophages, as well as non-hematopoietic cells, including neural cells, ganglion cells, epithelia cells, keratinocytes, muscle cells, pancreatic cells, and epithelial stem cells. In general, CD24 tends to be expressed at higher levels in progenitor cells and metabolically active cells and to a lesser extend in terminally differentiated cells. The function of CD24 is unclear in most cell types, but diverse immunological functions of CD24 have been reported.

CD24 interacts with Siglec-10 on innate immune cells to negatively regulates host response to cellular damage-associated with inflammation and at least two overlapping mechanisms may explain this activity. First, CD24 binds to several Damage Associated Molecular Patterns (DAMPs), including HSP70, 90, HMGB1 and nucleolin and represses host response to these DAMPs. It is presumed that CD24 may trap the inflammatory stimuli to prevent their interaction with TLR or RAGE. Second, through interaction with its receptor, Siglec G (the mouse homolog of Siglec-10), CD24 provides a powerful negative regulation for host response to tissue injuries. To achieve this activity, CD24 may bind and stimulate signaling by Siglec G wherein Siglec G-associated SHP1 triggers the negative regulation. Both mechanisms may act in concert as mice with targeted mutation of either gene mounted much stronger inflammatory response.

Siglecs are Type I transmembrane proteins where the $NH3^{+}$-terminus is in the extracellular space and the $COO^{-}$-terminus is cytosolic. The extracellular domain of Siglec-10 contains an N-terminal V-type immunoglobulin domain (Ig domain) which acts as the binding receptor for sialic acid and five C2-type Ig domains which have no binding activity but extend the V-type Ig binding domain away from the cell surface. The cytoplasmic domains of most Siglecs, including Siglec-10, have immunoreceptor tyrosine-based inhibitory motifs (ITIMs) and signal negatively via the recruitment of tyrosine phosphatases such as the SH2 domain containing protein tyrosine phosphatases SHP1 and SHP2. The primary function of Siglecs is to bind glycans containing sialic acids. These receptor-glycan interactions can be used in cell adhesion, cell signaling and other functions, which is often limited to their cellular distribution. Human Siglec-10 is the functional ortholog of mouse Siglec G and it binds both mouse and human CD24.

Many cancers avoid clearance by the immune system through the overexpression of antiphagocytic surface proteins called "do not eat me" signals. Examples of such proteins include PD-L1 and CD47, which bind to PD-1 and signal-regulatory protein α (SIRPα) on immune cells, respectively, which inhibit the activity of macrophages. Accordingly, antibodies that block or antagonize these do-not-eat-me pathways have been developed as immuno-oncology drugs. It has been demonstrated that CD24 represents yet another such do-not-eat-me signal through its interaction with Siglec-10 and, although CD24 is found in many normal tissues and cell types, CD24 is overexpressed in nearly 70% of human cancers and is one of the most overexpressed proteins in cancer cells. CD24 expression is upregulated during tumorigenesis, suggesting its role in tumor progression and metastasis. Overexpression of CD24 in cancer has also been identified as a marker indicative of poor prognosis and a more aggressive course of the disease for cancer patients.

Accordingly, there is a need in the art for new immunotherapies that target the CD24:Siglec-10 do-not-eat-me axis for the treatment of cancer.

SUMMARY OF THE INVENTION

Provided herein is an anti-Siglec-10 antibody, which may comprise: (a) a heavy chain variable region comprising one or more of a complementarity determining region (CDR) 1 comprising the sequence set forth in SEQ ID NO: 3, a CDR2 comprising the sequence set forth in SEQ ID NO: 4, and a CDR3 comprising the sequence set forth in SEQ ID NO: 5; and, (b) a light chain variable region comprising one or more of a CDR1 comprising the sequence set forth in SEQ ID NO: 6, a CDR2 comprising the sequence set forth in SEQ ID NO: 7, and a CDR3 comprising the sequence set forth in SEQ ID NO: 8. The heavy chain variable region may comprise the sequence set forth in SEQ ID NO: 1, and the light chain variable region may comprise the sequence set forth in SEQ ID NO: 2. The antibody may be a chimeric antibody.

The heavy chain variable region of the anti-Siglec-10 antibody may comprise the sequence set forth in one of SEQ ID NOS: 9-13, and the light chain variable region may comprise the sequence set forth in one of SEQ ID NOS: 14-18. The heavy chain variable region may comprise the sequence set forth in SEQ ID NO: 9, 10, or 11; and the light chain variable region may comprise the sequence set forth in SEQ ID NO: 15. The heavy chain variable region of the Siglec-10 antibody may comprise the sequence set forth in SEQ ID NO: 10 or 12; and the light chain variable region may comprise the sequence set forth in SEQ ID NO: 17. The heavy chain variable region of the anti-Siglec-10 antibody may comprise the sequence set forth in SEQ ID NO: 10 or 12; and the light chain variable region may comprise the sequence set forth in SEQ ID NO: 16. The antibody may comprise a heavy chain variable region comprising the sequence set forth in SEQ ID NO: 9 and a light chain variable region comprising the sequence set forth in SEQ ID NO: 15. The antibody may comprise a heavy chain comprising the sequence set forth in SEQ ID NO: 25, and may further comprise a light chain comprising the sequence set forth in SEQ ID NO: 27. The antibody may comprise a heavy chain variable region comprising the sequence set forth in SEQ ID NO: 10 and a light chain variable region comprising the sequence set forth in SEQ ID NO: 15 or 16. The antibody may comprise a heavy chain comprising the sequence set forth in SEQ ID NO: 32 and a light chain comprising the sequence set forth in SEQ ID NO: 27. The antibody may comprise a heavy chain comprising the sequence set forth in SEQ ID NO: 32 and a light chain comprising the sequence set forth in SEQ ID NO: 34.

Also provided herein is a method of treating a cancer in a patient in need thereof, which may comprise administering the anti-Siglec-10 antibody to the patient. Further provided are the anti-Siglec-10 antibody for use in treating a cancer, and use of the anti-Siglec-10 antibody in the manufacture of a medicament for treating a cancer. Also provided is a composition comprising the anti-Siglec-10 antibody for treating a cancer. The composition may be a pharmaceutical composition.

The anti-Siglec-10 antibody may be administered in combination with a second cancer therapy, or may be intended for use in combination with a second cancer therapy. The second cancer therapy may be a cancer-targeting immunotherapy or an immune-cell-targeting immunotherapy. The second cancer therapy may be an anti-CTLA-4 antibody.

The cancer may be an advanced solid tumor, a hematologic cancer, or a cancer that includes infiltrating cells that bind to the anti-Siglec-10 antibody. The cancer may be an advanced solid tumor, which may be a lung adenocarcinoma (LUAD), a skin cutaneous melanoma-metastasis (SKCM-TM), a lung squamous cell carcinoma (LUSC), a breast invasive carcinoma—basal, a breast invasive carcinoma—Her2, a pancreatic adenocarcinoma, a head and neck squamous cell carcinoma, a kidney renal clear cell carcinoma, a stomach adenocarcinoma, a glioblastoma multiforme, a breast invasive carcinoma—LumB, or a breast invasive carcinoma—LumA, a non-small cell lung cancer, a glioblastoma, a melanoma, a low grade glioma, a kidney cancer, a breast cancer basal type, a Her2+ breast cancer, a pancreatic cancer, or an ovarian cancer. The lung adenocarcinoma may be a non-small cell lung adenocarcinoma. The hematologic cancer may be a leukemia, a myeloid dysplasia syndrome, a B cell lymphoma, or a multiple myeloma.

BRIEF DESCRIPTION OF THE DRAWINGS

FIG. 4A. Flow chart of experimental protocol.

FIG. 4B. % of inhibition of Siglec-10Fc (S10) binding to spleen cells.

FIG. 6A. Kinetics of tumor growth. FIG. 6B. % of tumor bearing mice over time.

TABLE 1

| Tm of humanized 31F11 clone | | | | | | |
|---|---|---|---|---|---|---|
| | | Tm1 | | | Tm2 | |
| Chimeric | 65.8 | 65.8 | 65.8 | | | |
| #21 | 63.6 | 63.7 | 63.7 | 78.6 | 78.5 | 78.5 |
| #22 | 63.7 | 63.8 | 63.8 | 78.5 | 78.5 | 78.5 |
| #23 | 64 | 64 | 63.9 | 80.6 | 80.7 | 80.6 |
| #32 | 67 | 66.6 | 67 | | | |
| #34 | 64.5 | 64.4 | 64.4 | 71.6 | 71.7 | 71.7 |
| #52 | 66.7 | 66.6 | 66.6 | | | |
| #54 | 69.2 | 68.9 | 69.2 | | | |

Figure 9:
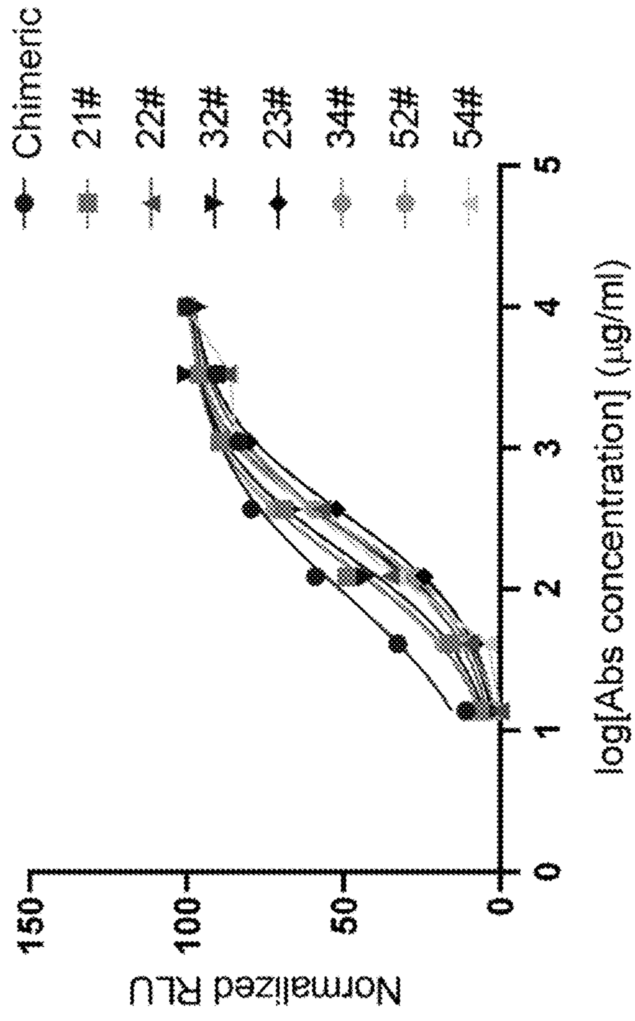

FIG. 9 shows antagonist activities of humanized 31F111 clones based on their activity in rescuing antibody-dependent cell-mediated cytotoxicity (ADCC) reporter assay. $5\times10^4$ Jurkat-PWPI-S10 cells and $5\times10^4$ CHO-hCTLA4 cells were co-cultured with 0.1 μg/ml anti-hCTLA4 and anti-siglec 10 antibodies of the indicated concentrations. After 16-24 hours incubation, BIO-GLO™ Luciferase Assay Reagent was added to all the test wells and luminescence was measured using a plate reader with glow-type luminescence read capabilities. Data shown are % of maximal ADCC activities over grading doses of antibodies.

Figure 10A:
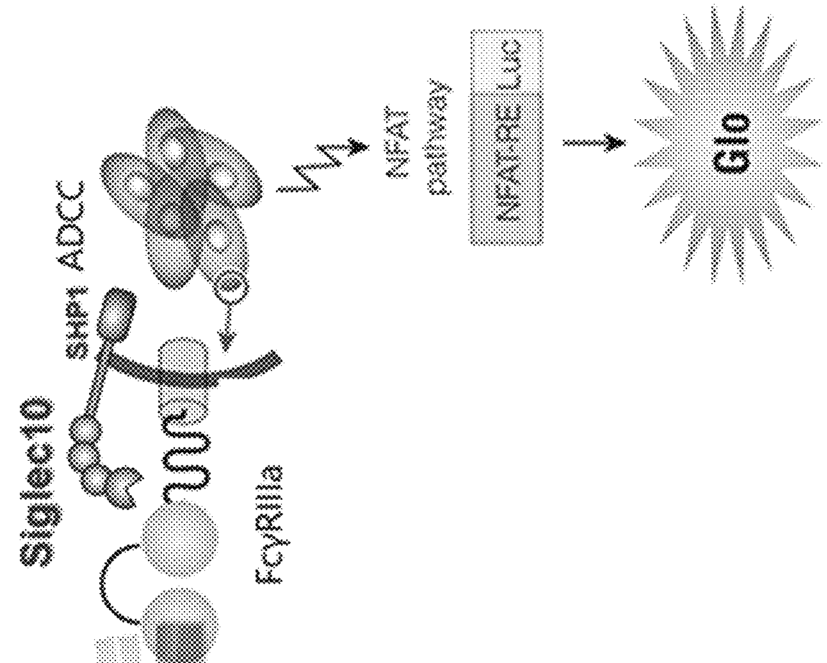
Figure 10B:
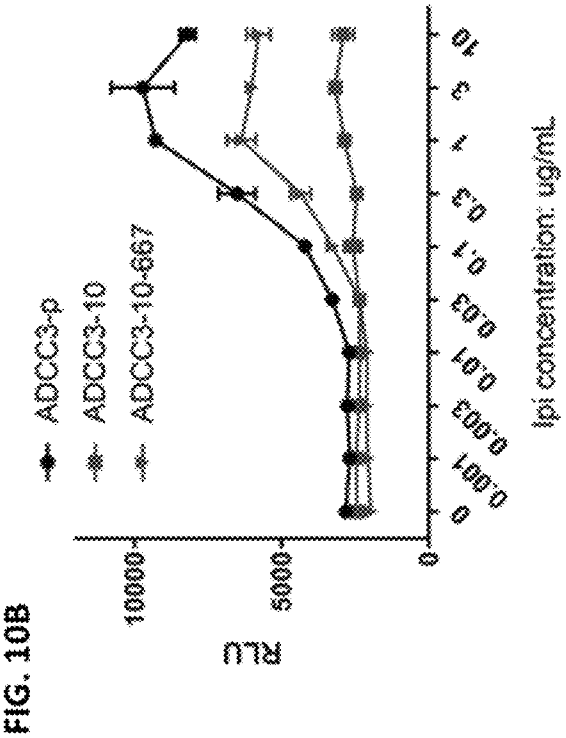

FIGS. 10A-B show Siglec-10 signaling suppresses ADCC reporter activity. FIG. 10A. Diagram of the reporter assay. Jurkat reporter cells activates NFAT expression upon activation of FcγRIIIA in the presence of CTLA-4 expressing target cell and varying concentration of the anti-CTLA-4 mAb, Ipilimumab. FIG. 10B. Reporter activity of Jurkat reporter cells expressing vector control (ADCC3-p), WT Siglec-10 protein (ADCC3-10) or mutant Siglec-10 with a Y>A mutation in ITIM domain position 667, which partially prevent negative signaling by Siglec-10 (ADCC3-10-667).

Figure 11:
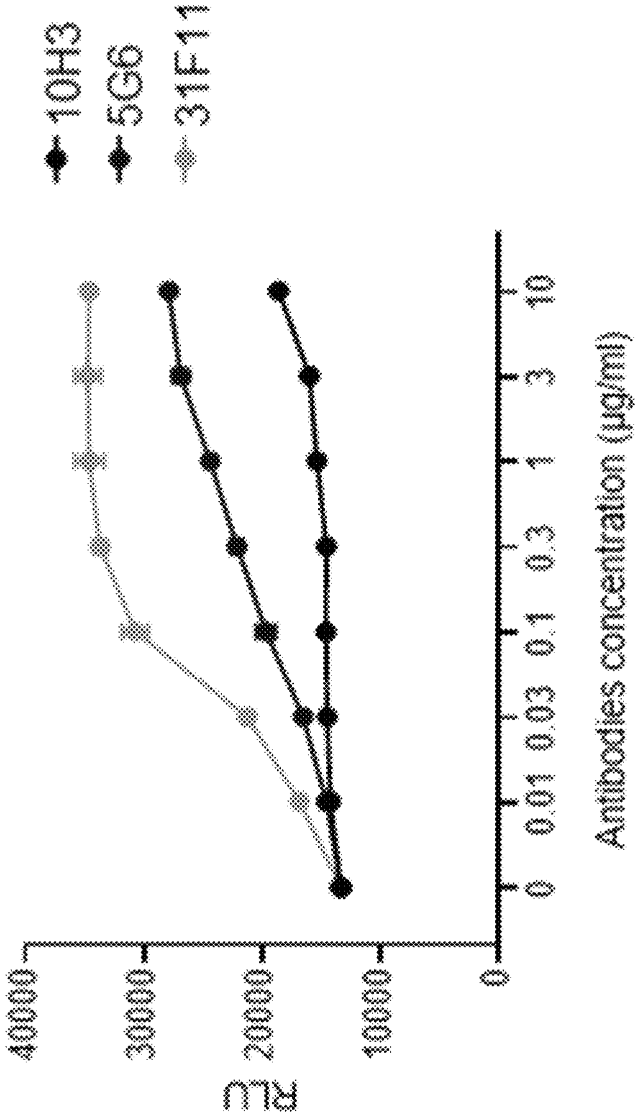

FIG. 11 shows superior activity of 31F111 in enhancing ADCC activity. Siglec-10-expressing Jurkat reporter cells, ADCC3-10, were used as reporter cells. CTLA-4 expressing CHO cells were used as target cells. Cells were co-cultured in the presence of 0.1 μg/mL of anti-CTLA-4 mAb ONC-392 and serial diluted anti-Siglec-10 mAbs 10H3, 5G6 and 31F11. The assay design is diagramed in FIG. 10A. Given doses of 3 anti-Siglec-10 mAbs were compared.

Figure 12:
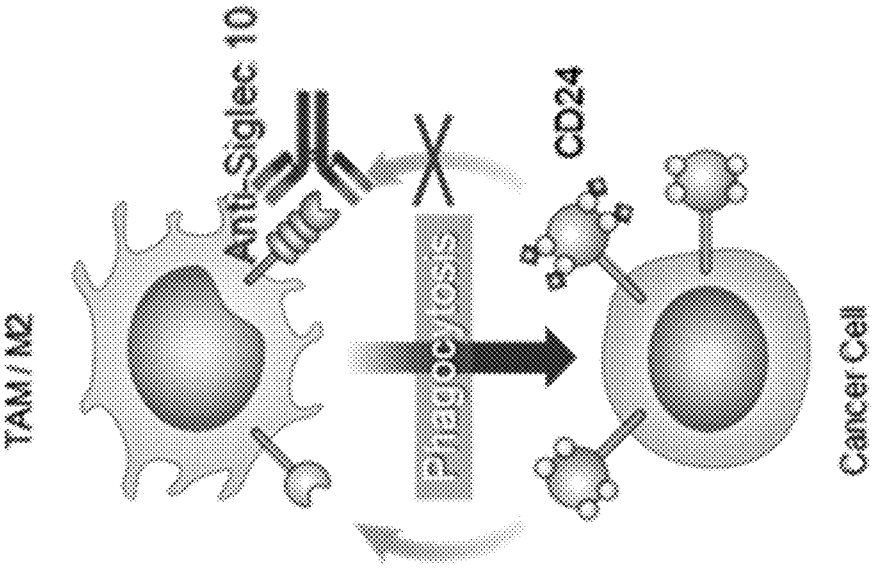

FIG. 12 shows a schematic of how ONC-841 is thought to block do-not-eat-me signals (DNEMS) by CD24-Siglec-10 to promote phagocytosis of tumor cells.

Figure 13:
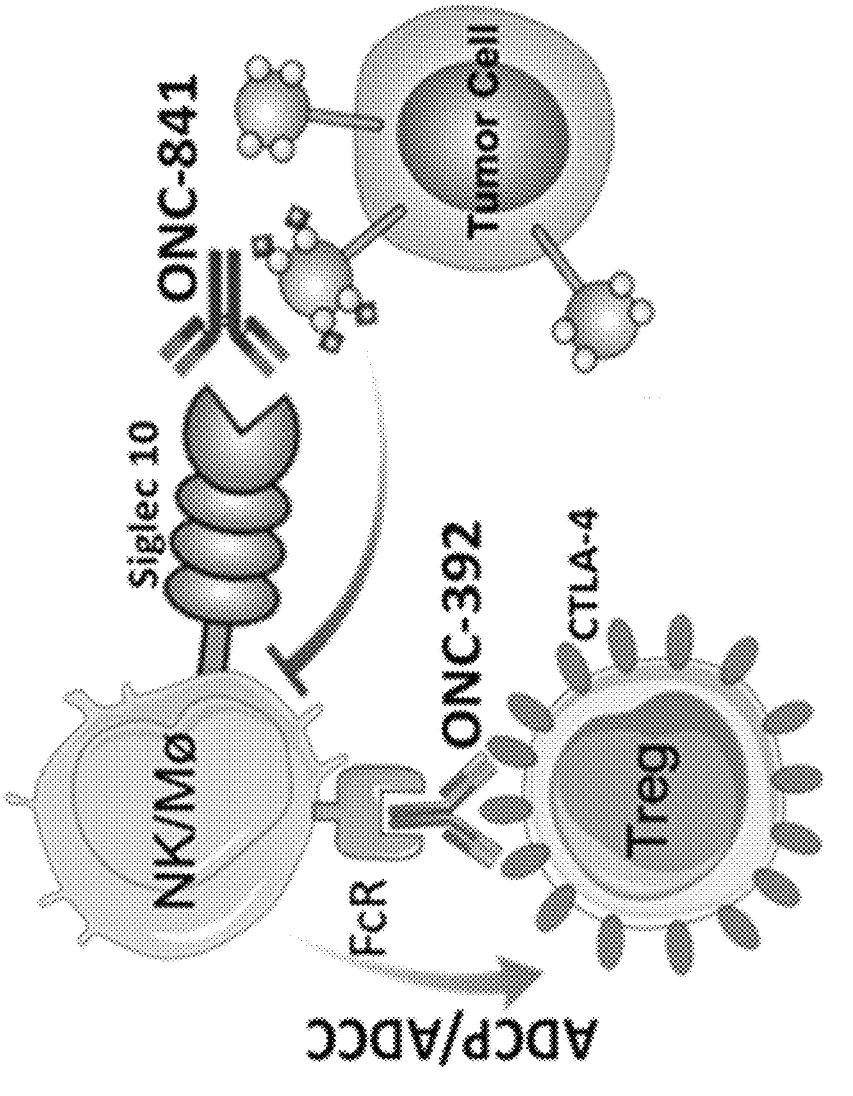

FIG. 13 shows the mechanism of ONC-841 in combination therapy with ONC-392. ONC-392 causes tumor rejection by selectively depleting Treg in the tumor microenvironment, thereby enhancing the intratumoral T cell response; while ONC-841 enhances ADCC/ACDP-mediated Treg depletion by antagonizing Siglec-10 mediated suppression.

Figure 14B:
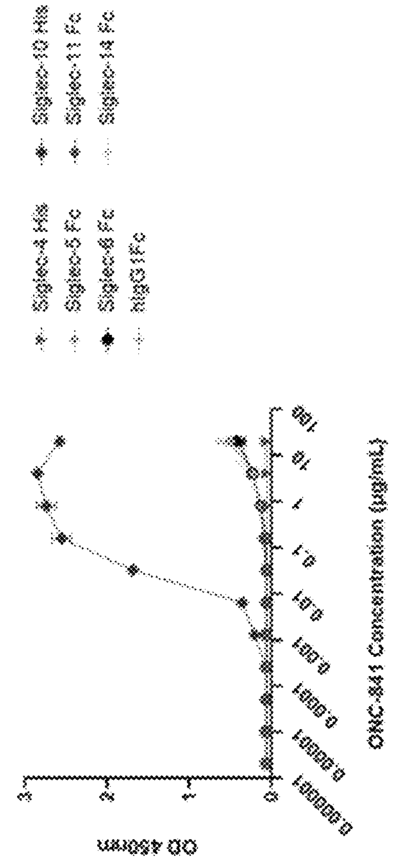
Figure 14A:
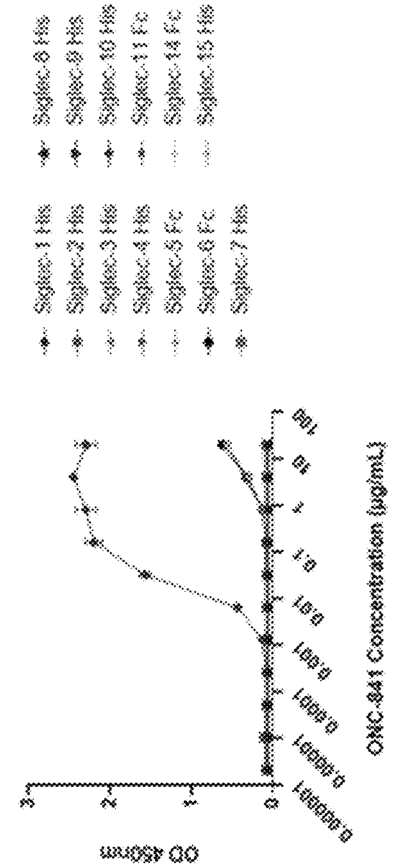

FIGS. 14A-B show binding of ONC-841 to recombinant Siglec family proteins. FIG. 14A. Specificity of ONC-841 to His-tagged or Fc-tagged Siglecs. FIG. 14B. ONC-841 showed binding to human IgG1Fc at high concentration in similar pattern to Siglec-5Fc, Siglec-6Fc, Siglec-11Fc and Siglec-14Fc, suggested that binding of ONC-841 to Siglec-5Fc, Siglec-6Fc, Siglec-11Fc and Siglec-14Fc is due to non-specific binding to the Fc tag and not specific binding to recombinant Siglec proteins.

Figure 15:
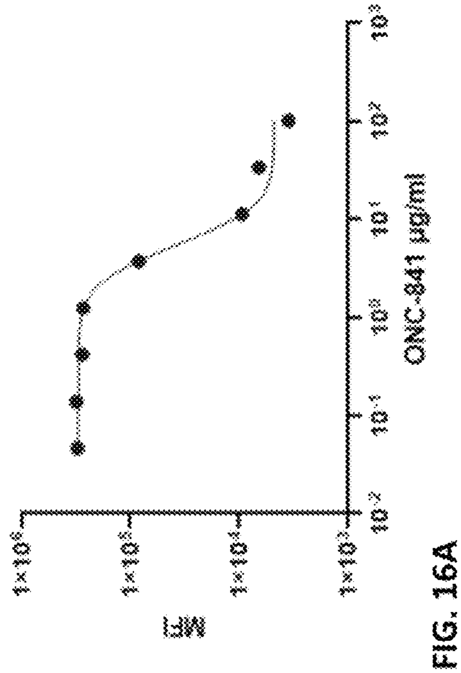

FIG. 15 shows ONC-841 blocks binding of Siglec-10Fc to Jurkat-CTLA4 cells. Siglec-10 Fc-biotin was pre-complexed with streptavidin-PE and incubated with increasing concentrations of ONC-841 for 5 min prior to incubation with Jurkat-CTLA4 cells for 1 hour.

Figure 16A:
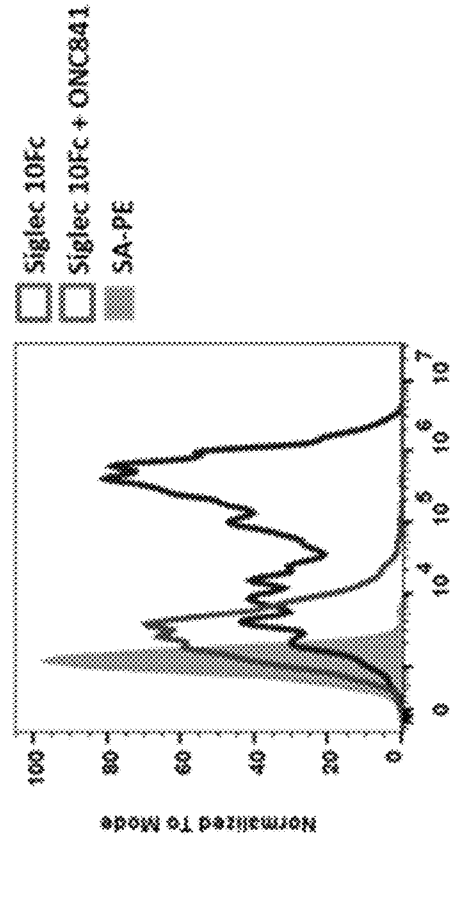
Figure 16B:
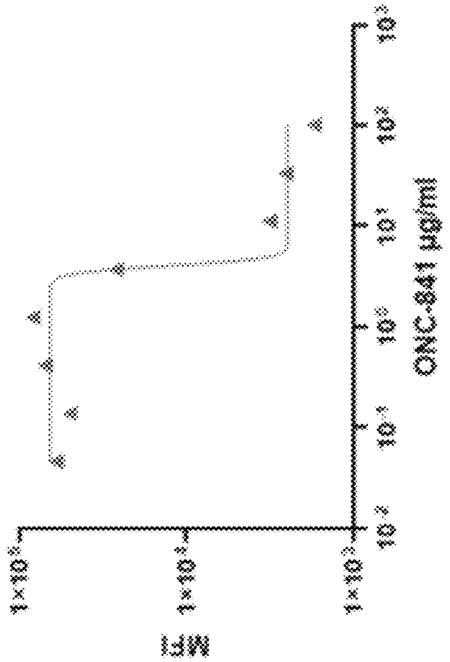

FIGS. 16A-B show the effect of ONC-841 on Siglec-10Fc binding to Treg. FIG. 16A. Representative data showing Siglec-10-biotin+streptavidin-PE binding to Treg with (lighter grey) or without (darker grey) 100 μg/mL of ONC-841. Streptavidin-PE is shown in grey as a negative control. FIG. 16B. Non-linear regression analysis of ONC-841 blockade of Siglec-10Fc-biotin+streptavidin-PE binding to Treg.

Figure 17B:
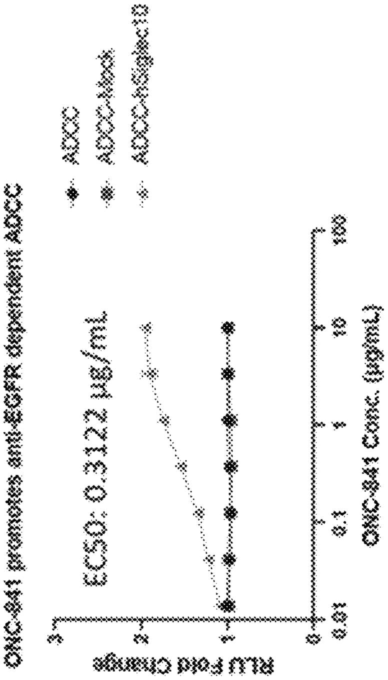
Figure 17A:
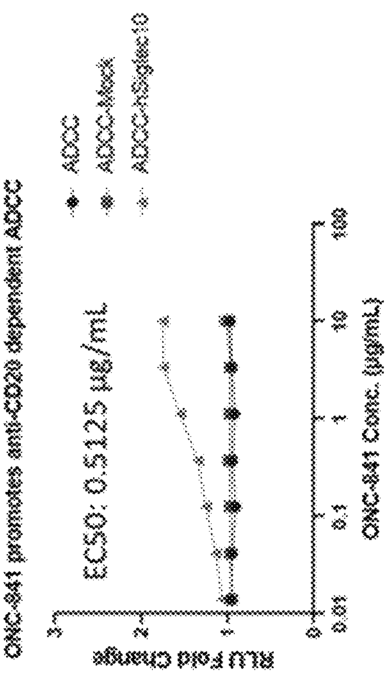
Figure 17C:
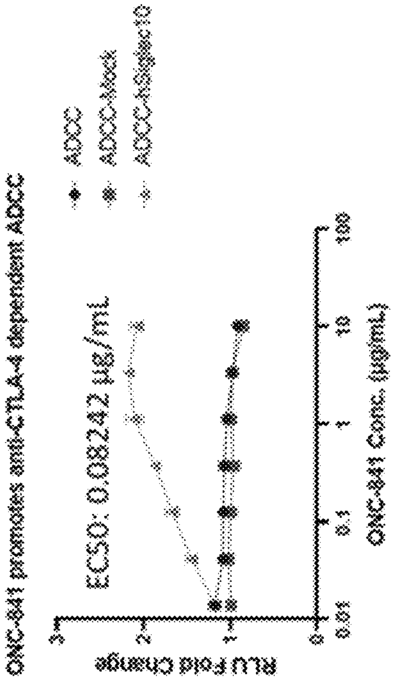

FIGS. 17A-C show the effect of ONC-841 in antibody-dependent ADCC reporter assay. FIG. 17A. ONC-841 promotes anti-CD20 dependent ADCC against Raji cells. FIG. 17B. ONC-841 promotes cetuximab dependent ADCC against EGFR expressing B16 cells. FIG. 17C. ONC-841 promotes ONC-392 dependent ADCC against CTLA-4 expressing CHO cells. Data shown is normalized to show the fold increase in ADCC activity over baseline.

Figure 18C:
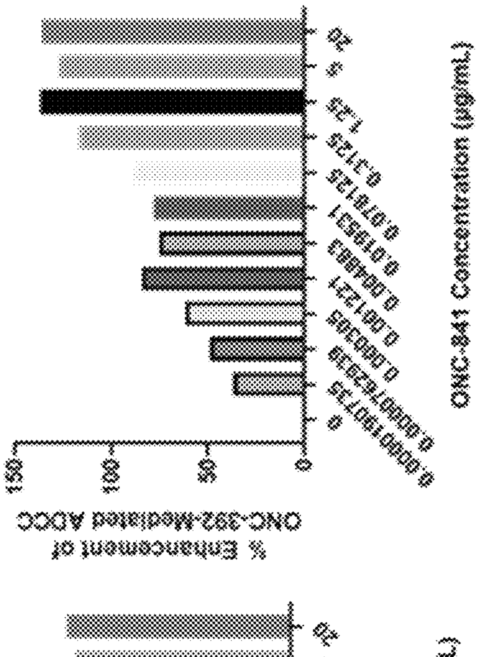
Figure 18B:
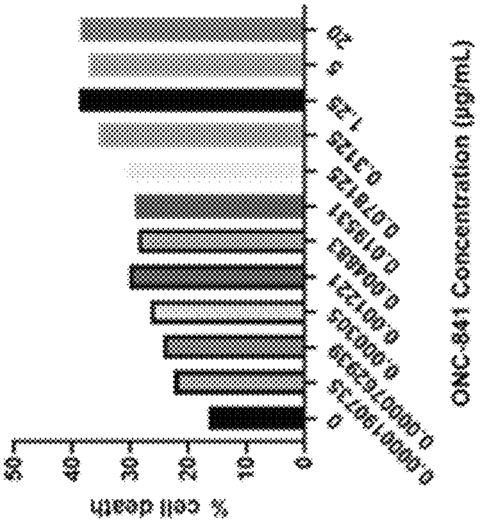
Figure 18A:
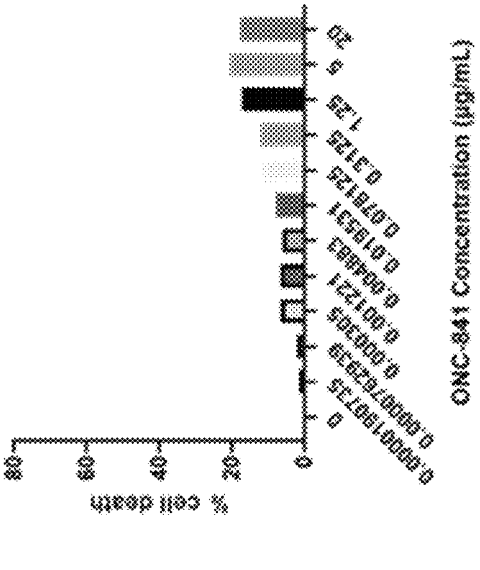

FIGS. 18A-C show the effect of ONC-841 in ADCC and antibody independent killing of leukemia cells by human NK cells. FIG. 18A. Without ONC-392. FIG. 18B. With ONC-392. FIG. 18C. % enhancement of ONC-392 mediated ADCC by ONC-841.

Figure 19:
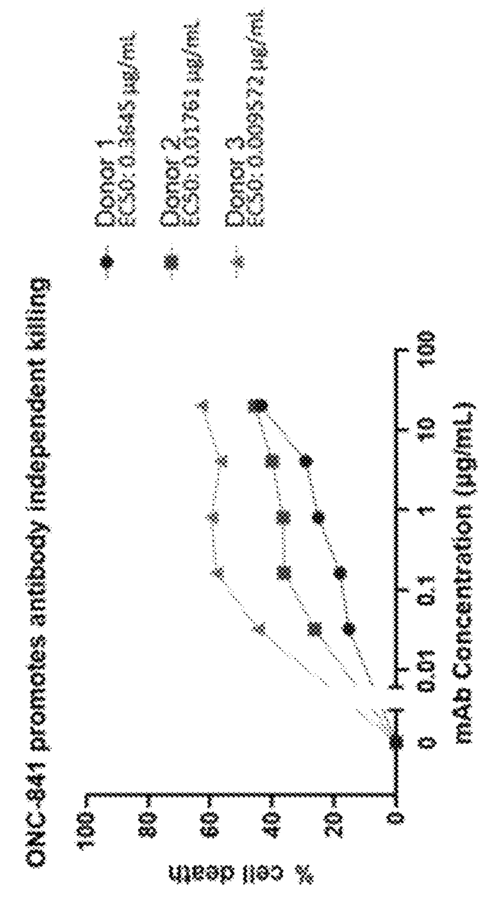

FIG. 19 shows the effect of ONC-841 in antibody-independent killing of leukemia cells by human PBMCs. ONC-841 promotes PBMC killing of Jurkat-CTLA-4 cells in the absence of cancer cell targeting antibody.

Figure 20:
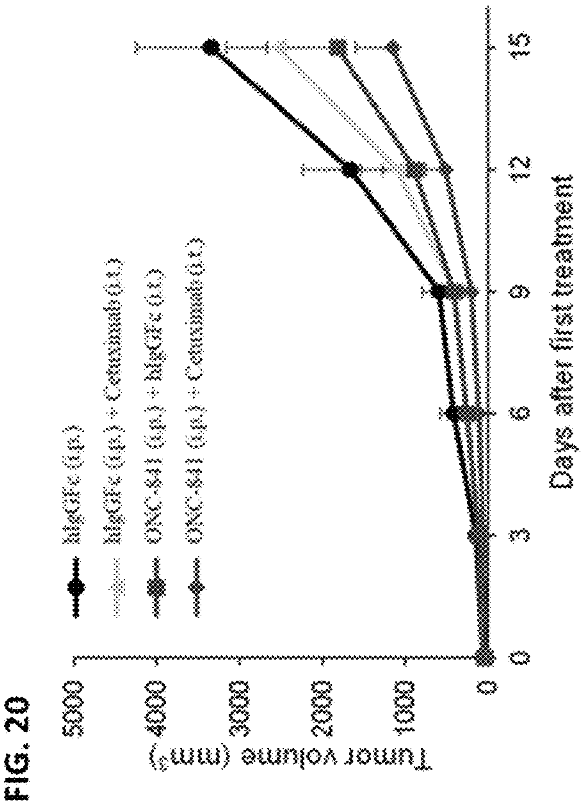

FIG. 20 demonstrates the therapeutic activity of ONC-841 in solid tumors. A B16F10 cell line expressing human EGFR was used. At 6 days after tumor cell challenge, tumor-bearing mice were treated with control IgG, ONC-841 or ONC-841+cetuximab, and tumor growth was measured in a blinded fashion. B16-EGFR tumor-bearing (s.c.) Siglec10TG$^{+/+}$; Siglecg$^{-/-}$ mice (n=4-5) were treated intraperitoneally (i.p.) with 200 μg of control hIgGFc or ONC-841 and intratumorally (i.t.) with 10 μg of control hIgGFc or Cetuximab every three days for four injections, starting on day 6 after tumor inoculation.

Figure 21B:
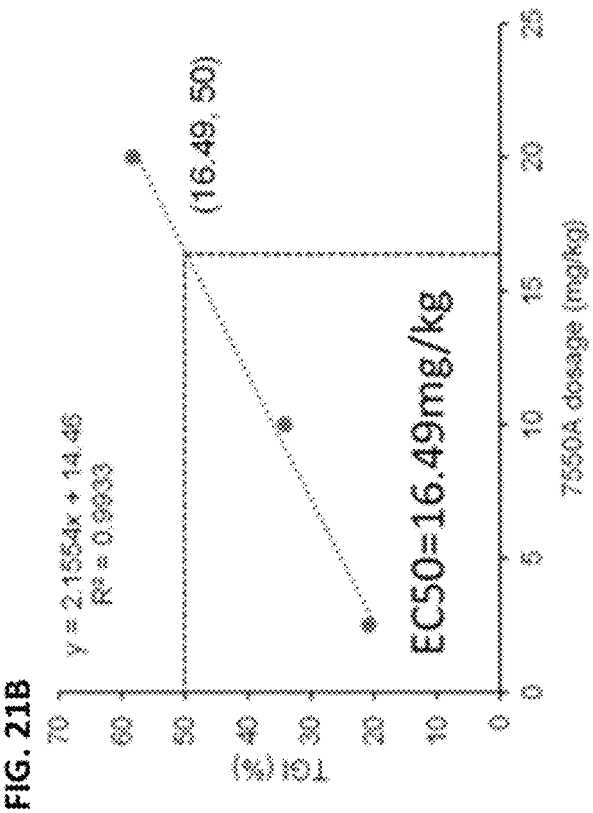
Figure 21A:
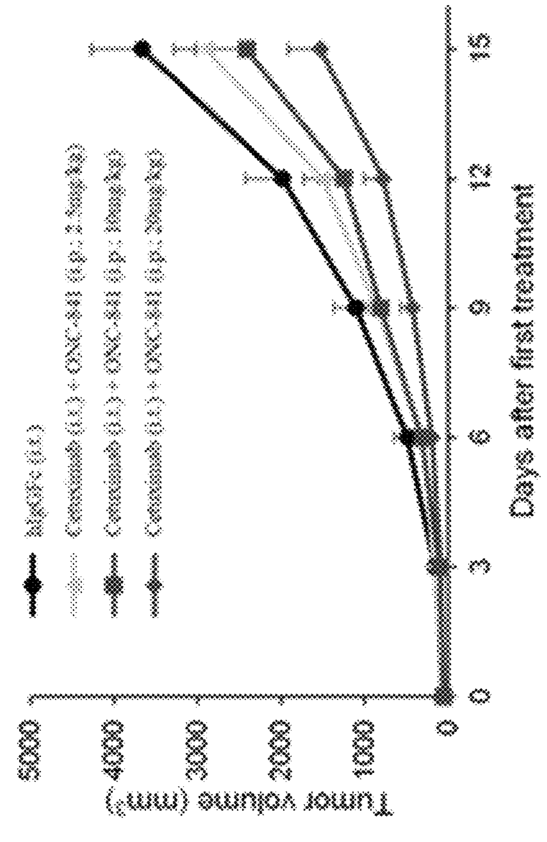

FIGS. 21A-B show dose response of ONC-841 in combination therapy. FIG. 21A. Tumor growth kinetics. FIG. 21B. Linear regression analysis to determine $EC_{50}$ using the data from the last time point in FIG. 21A.

Figure 22:
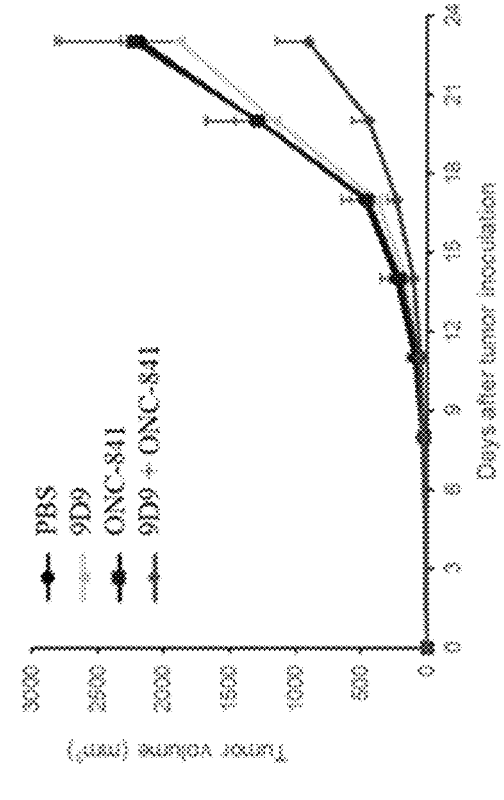

FIG. 22 shows the combination of ONC-841 and anti-CTLA-4 antibody 9D9 causes rejection of B16F10 melanoma cells. B16-F10 tumor-bearing C57BL/6 SIGLEC10TG$^{+/+}$; Siglecg$^{-/-}$ mice (n=5-6) were treated i.p. with 200 μg of 9D9 or/and 400 μg of ONC-841 on day 8, 11, 14 and 17. Tumor volumes were measured every 3 days. Data shown are means and SEM.

Figure 23:
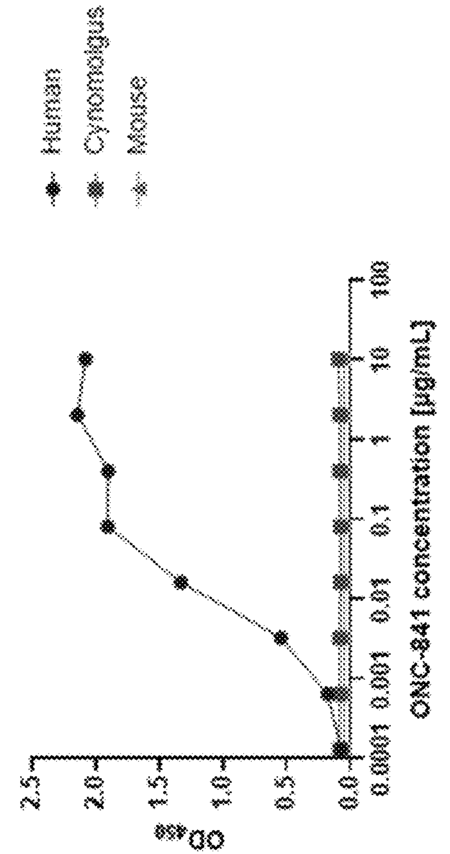

FIG. 23 shows a colorimetric ELISA assay to detect binding of ONC-841 to His-tagged Siglec-10/Siglec-G from different species.

Figure 24:
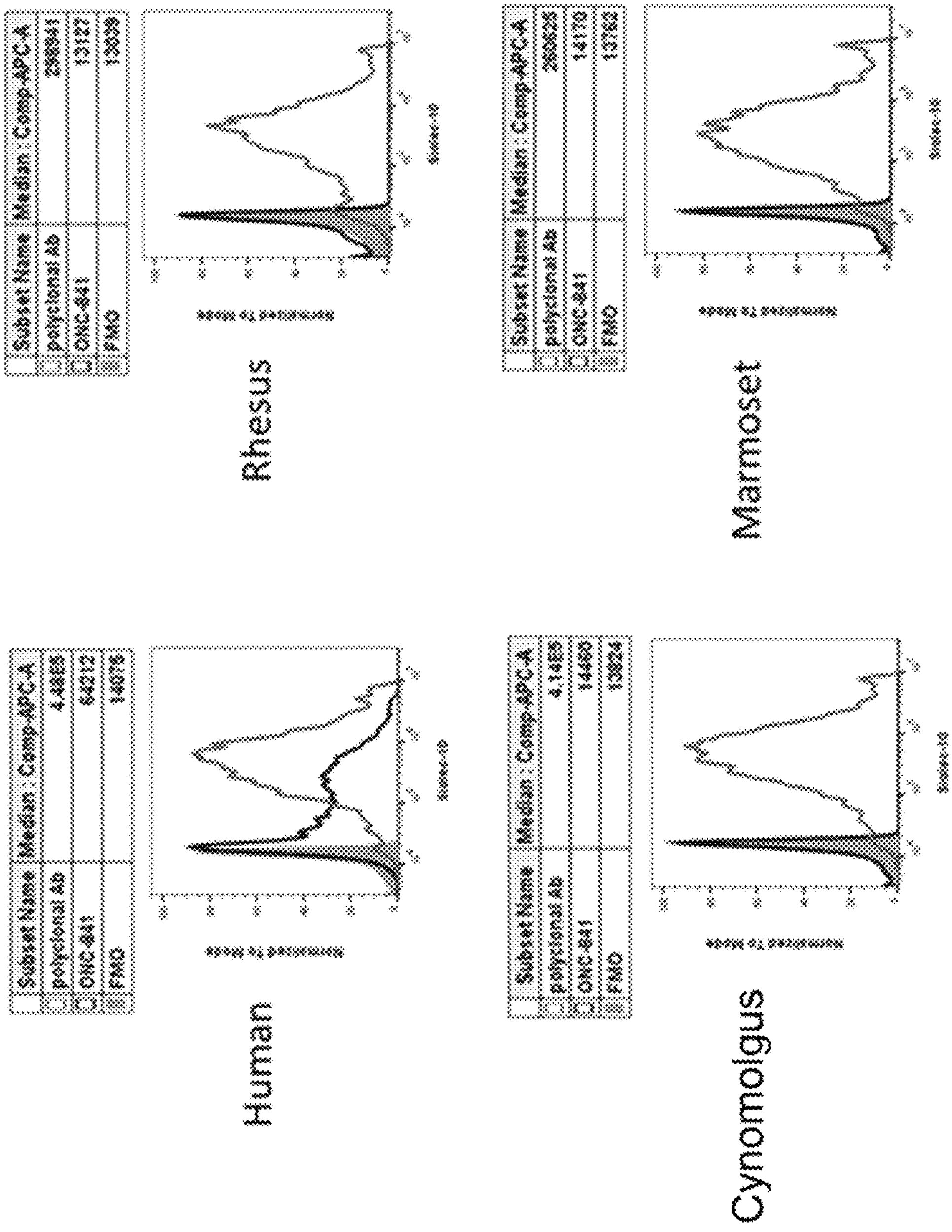

FIG. 24 shows flow cytometry evaluation of binding of ONC-841 to Siglec-10 orthologs expressed on expi293. Live cells were gated using Zombie dye, and binding of ONC-841 (darker grey lines) was evaluated and compared to polyclonal anti Siglec-10 antibodies (lighter grey lines). Fluorescent-minus-one (FMO, gray) was used as negative control. Numbers in the legends of each histogram show the median fluorescent intensity for each sample.

Figure 25:
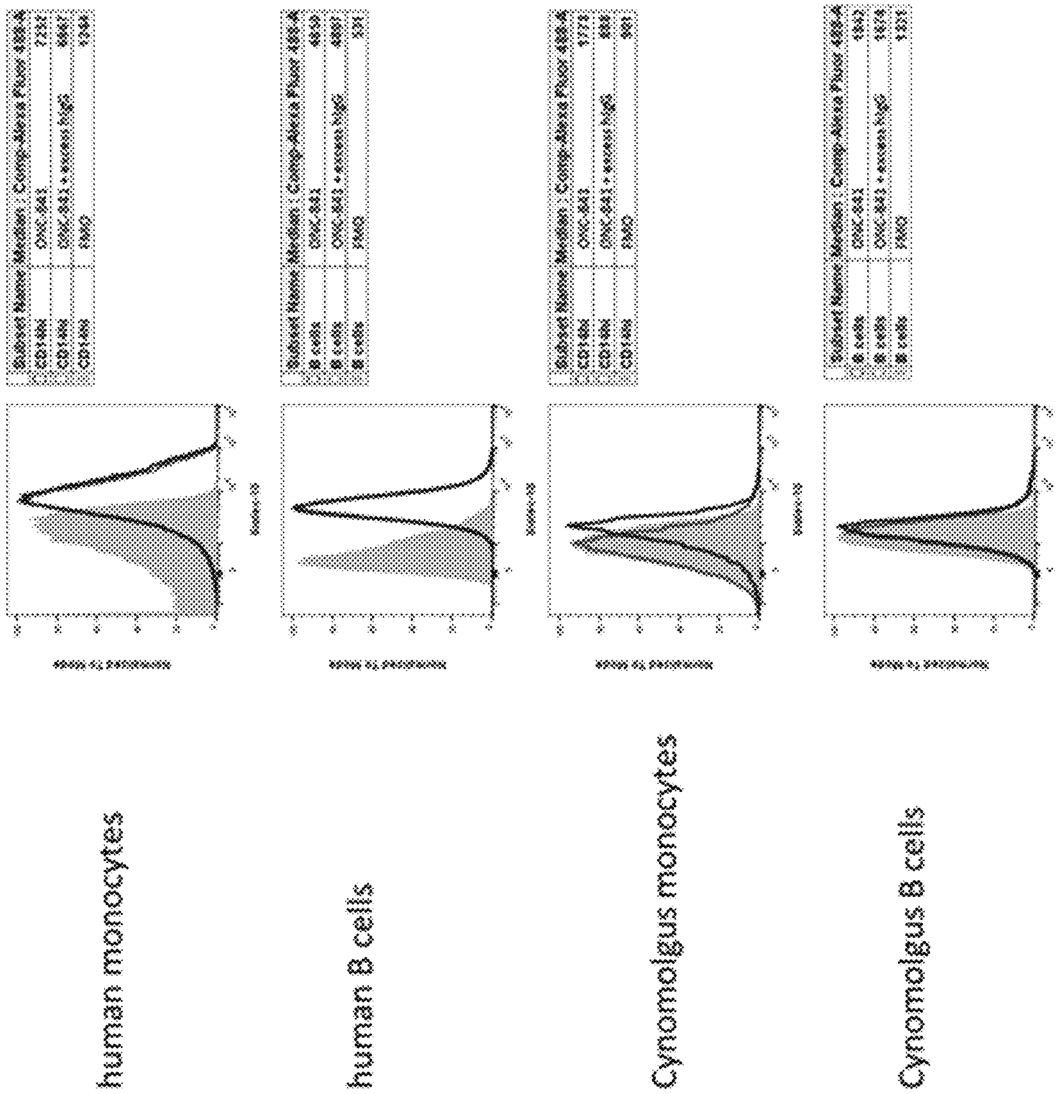

FIG. 25 shows flow cytometry evaluation of binding of ONC-841 to human and cynomolgus monocytes and B cells. Live cells were gated using Zombie dye, and binding of ONC-841 (darker grey lines) was evaluated and compared to a Fluorescent-minus-one (FMO, gray) as negative control. To test whether the binding is specific, an excess of human IgG was added to some of the tubes (lighter grey lines) before staining. Numbers in legend of each histogram show the median fluorescent intensity for each sample.

Figure 26B:
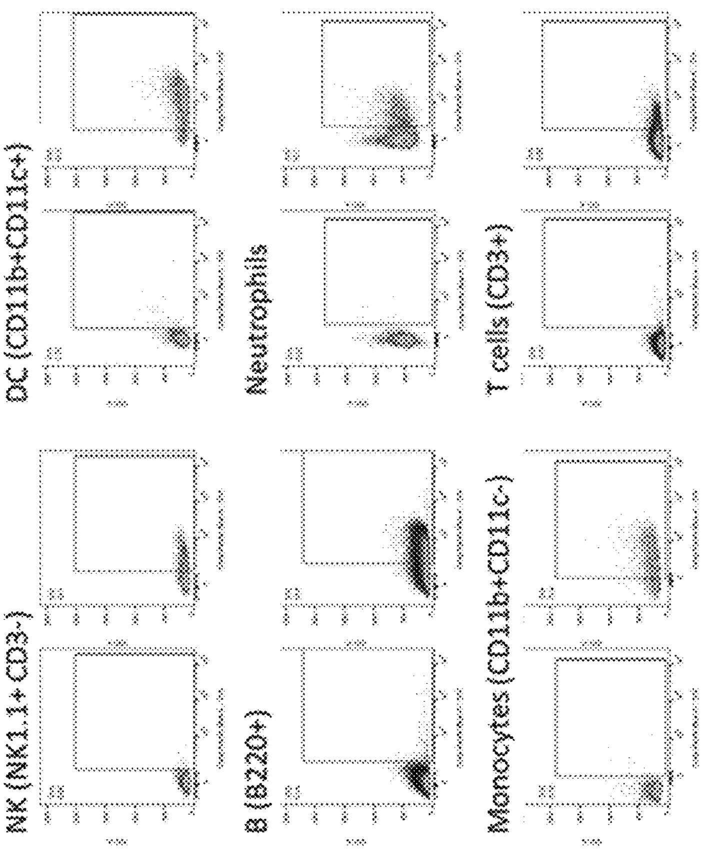
Figure 26A:
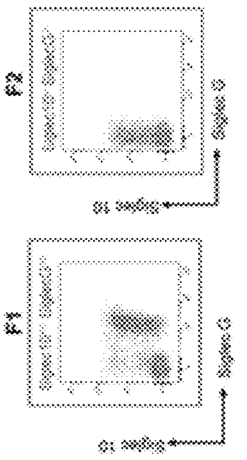
Figure 26C:
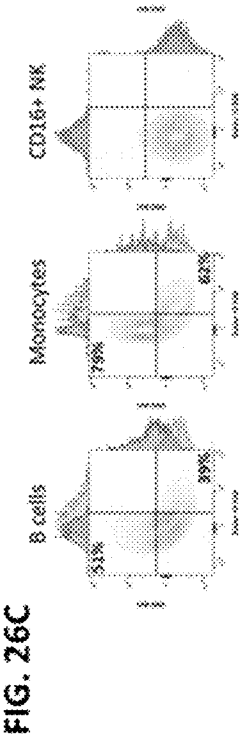

FIGS. 26A-C show binding of ONC-841 to Siglec10 transgenic mice and human PBMC. FIG. 26A. Left, Blood analysis from F1 mice from crossing human Siglec10 transgenic mice with SiglecG knockout mice. Mice express both human Siglec-10 and Siglec G. Right, blood analysis of crossing F1 mice and the phenotype of mice that were selected to generate the transgenic colony. F2 mice with only human Siglec-10 staining is selected for further breeding. Mouse blood was stained with commercially available antibodies. FIG. 26B. Additional staining of mouse blood subsets: NK cells, B cells, Dendritic cells (DC), Neutrophils, monocytes and T cells. Siglec-10 staining is shown on the X-axis, and for each cell subtype staining of non-transgenic mouse shown on the left graph and staining of human Siglec-10 transgenic mouse is shown on the right graph. FIG. 26C. Representative staining of human PBMC. ONC-841 on the Y-axis (lighter grey), commercially available 5G6 anti-Siglec-10 mAb antibody on the X-axis (darker grey), Each plot has an adjacent histogram showing the staining of each antibody alone. Percentages of positive cells are shown for B cells and monocytes which were positive for Siglec-10.

Figure 27:
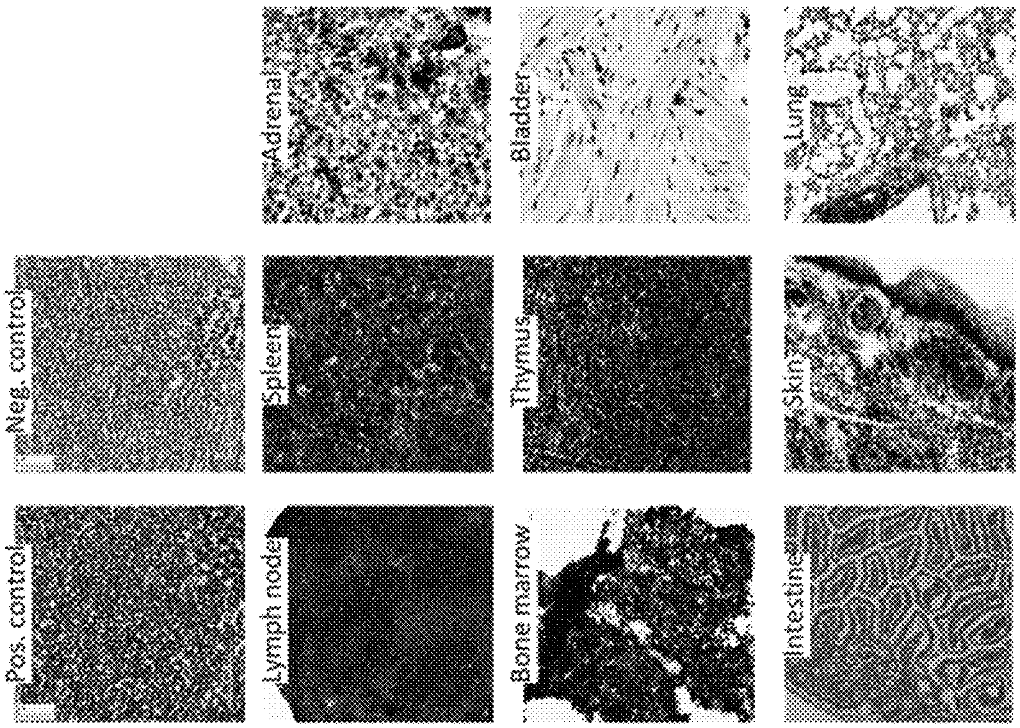

FIG. 27 shows immunohistochemical staining of frozen sections from different organs of Siglec10TG$^{+/+}$; Siglecg$^{-/-}$ mice. Top row shows positive and negative staining of Siglec-10 expressing (left) and Siglec-10 negative (right) cell pellets. Brown shows binding of ONC-841, blue is nuclear staining (Hematoxylin). All sections are shown in 20× magnification.

Figure 28:
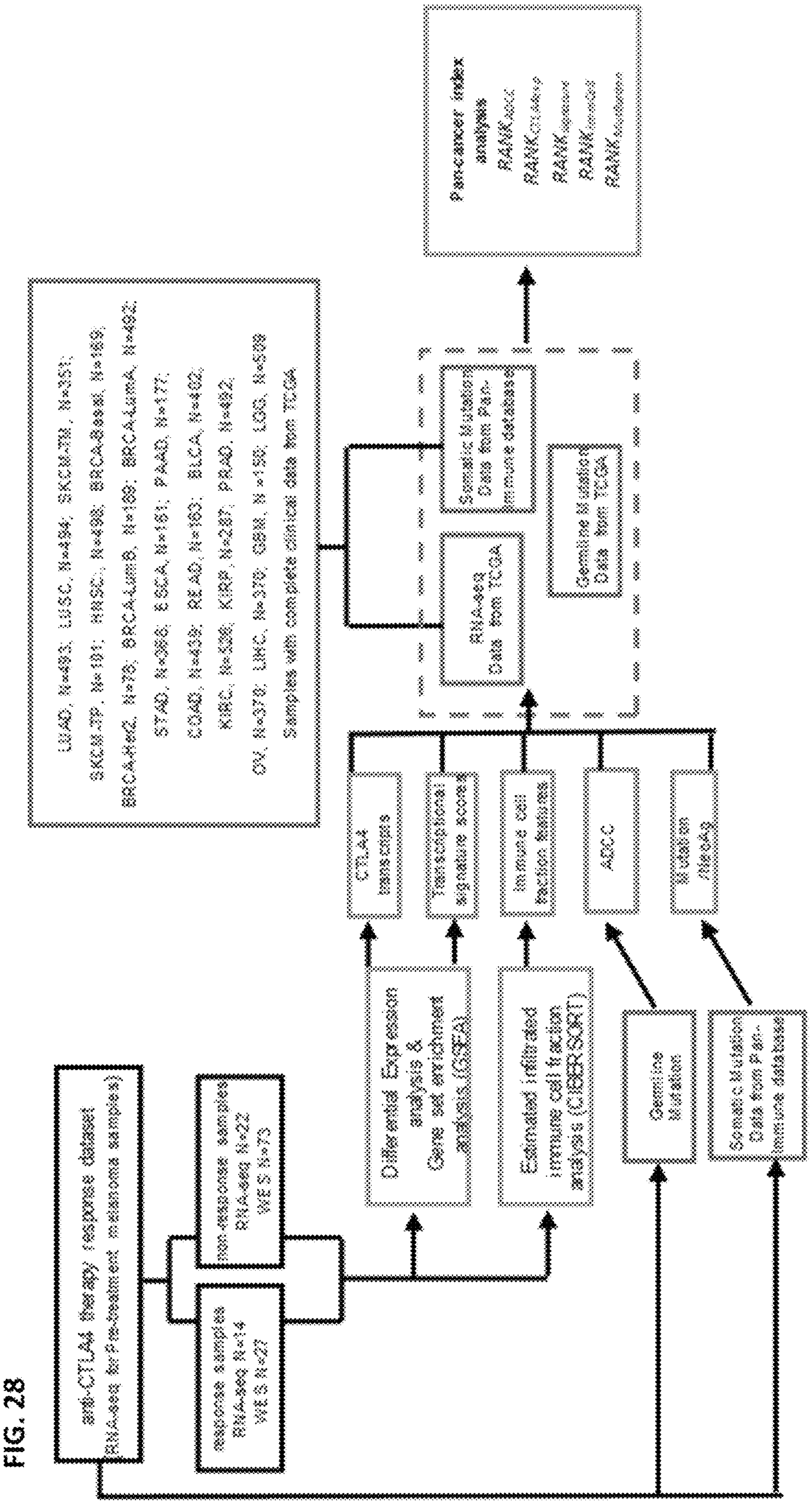

FIG. 28 shows a diagram of strategy to rank human cancer for their responsiveness to anti-CTLA-4 antibody treatment. We first identified components affecting therapeutic response of anti-CTLA-4 antibodies based on CTLA-4 response database, taking into consideration of newly identified mechanism of action by ant-CTLA-4 antibodies and analysis performed by another group on FCGR3A polymorphism and responsiveness to Ipilimumab. The human cancer types were ranked based on median value of each components. These components were weighted equally and grouped into 5 categories and ranked on each category. The rankings of the five categories were then weighted to yield a final ranking.

Figure 29:
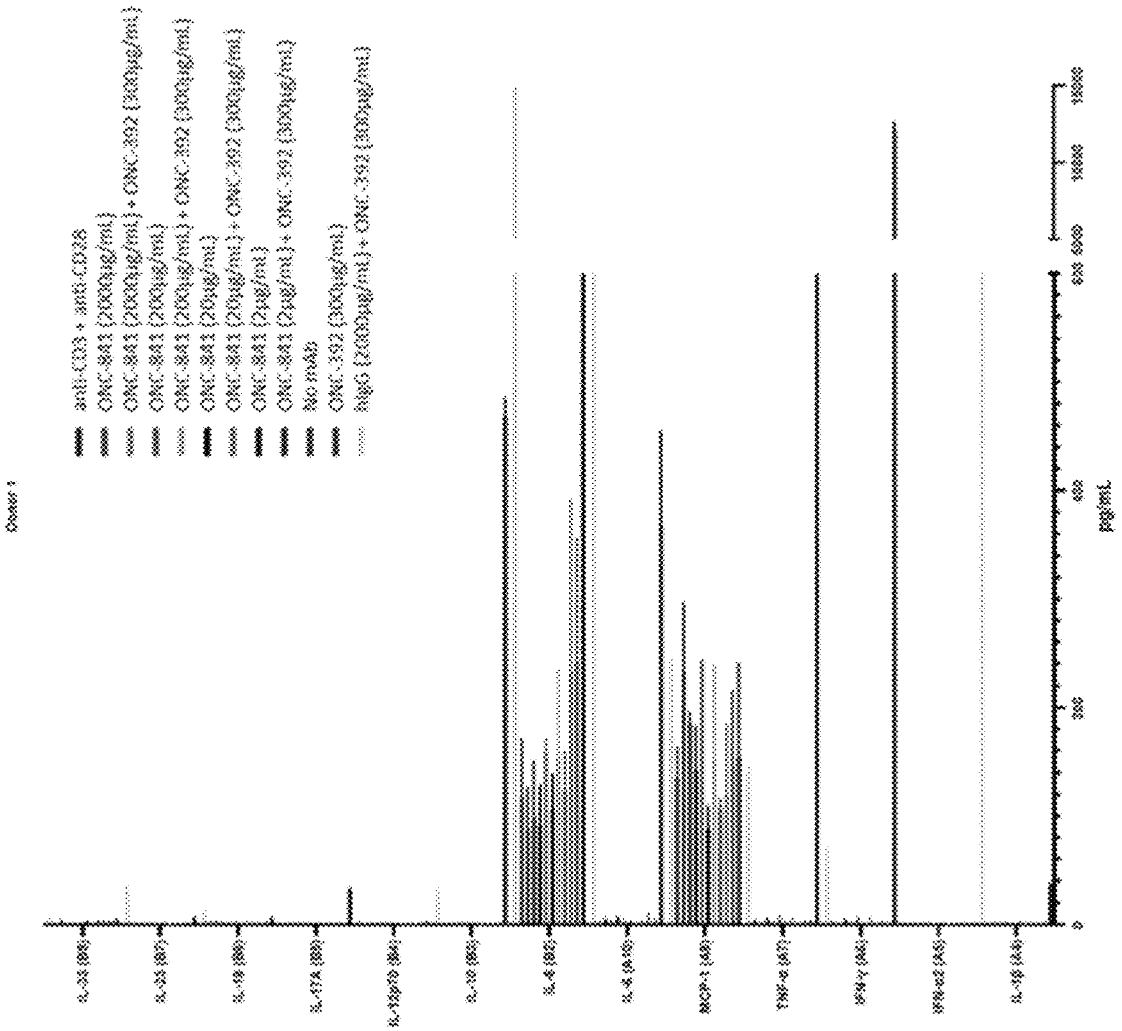

FIG. 29 shows that ONC-841 does not induce cytokine release syndrome (CRS). Representative data from one out of 4 donors is shown. Assay was done in duplicate.

DETAILED DESCRIPTION

The immune system can recognize and eliminate cancers in experimental model systems and in patients. As a result, cancer immunotherapies are emerging as one of the most promising areas of cancer therapy. Active cancer immunotherapies involve agents that amplify natural immune responses by blocking immune checkpoints or do-not-eat-me signals (including antibodies against PD-1, PD-L1, CTLA-4 and CD47).

Provided herein are anti-Siglec-10 antibody compositions of matter and antigen binding fragments thereof. The antibody molecule may be a monoclonal antibody, a human antibody, a chimeric antibody or a humanized antibody. The antibody may be monospecific, bispecific, trispecific or multispecific. The Siglec-10-binding molecule may comprise an antigen-binding fragment of an antibody that immunospecifically binds to Siglec-10, and in particular human Siglec-10, which in particular may be expressed on the surface of a live cell at an endogenous or transfected concentration. Also provided are antibody molecules of which the antigen-binding fragment binds to Siglec-10. The antibody may be detectably labeled or comprise a conjugated toxin, drug, receptor, enzyme, or receptor ligand.

Responsiveness of different tumor types and patients varies, which means that different inhibitory pathways may be relevant to different tumor types or different populations. Therefore, the identification of additional do-not-eat-me signals can lead to the development of new therapies that are more effective for certain tumor types or patients, either alone or possibly in combination. The antibody molecules described herein may be used to treat cancers by administering an anti-Siglec-10 antibody as described herein, either alone or in combination with other therapies.

The inventors have discovered anti-Siglec-10 antibodies that exhibit surprisingly potent binding to Siglec-10, particularly on the cell surface. The antibodies also enhance strong ADCC activities by inhibiting a potent do-not-eat-me signal.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise. The word "about" in association with a numeric value denotes a reasonable approximation of that value. In certain cases "about" may be construed as being within as much as 10% of the specific value with which it is associated. For example, the phrase "about 100" would encompass any value between 90 and 110.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Treatment" or "treating," when referring to protection of an animal from a disease, means preventing, suppressing, repressing, or completely eliminating the disease. Preventing the disease involves administering a composition of the disclosure to an animal prior to onset of the disease. Suppressing the disease involves administering a composition of the disclosure to an animal after induction of the disease but before its clinical appearance. Repressing the disease involves administering a composition of the disclosure to an animal after clinical appearance of the disease.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelid antibodies, single chain antibodies, disulfide-linked Fvs (sdFv), intrabodies, and anti-idiotypic (anti-Id) antibodies (including, e.g., anti-Id and anti-anti-Id antibodies to antibodies disclosed herein). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's CDR and optionally the framework residues that comprise the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.).

A "chimeric antibody" is a molecule in which different portions of the antibody are derived from different immunoglobulin molecules such as antibodies having a variable region derived from a non-human antibody and a human immunoglobulin constant region. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089, the contents of each of which are incorporated herein in their entirety), veneering or resurfacing (EP 592,106; EP 519,596, the contents of each of which are incorporated herein by reference), and chain shuffling (U.S. Pat. No. 5,565,332, the contents of which are incorporated herein by reference).

Also contemplated herein are "humanized antibodies." As used herein, the term "humanized antibody" refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. The donor antibody may be referred to as having been "humanized," by the process of "humanization," because the resultant humanized antibody is expected to bind to the same antigen as the donor antibody that provides the CDRs. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

2. Anti-Siglec-10 Antibody Compositions

Provided herein is an anti-Siglec-10 antibody or antigen binding fragment thereof. It is understood that one more features of the antibodies described herein may also be included in an antigen binding fragment. The anti-Siglec-10 antibody may bind to tumor-associated macrophages and may inhibit binding or signaling to CD24 expressed on cancer cells, thus inhibiting the anti-phagocytic signal from the cancer cells. The anti-Siglec-10 antibody may be a monoclonal antibody, single chain antibody, a bi-specific antibody, tri-specific antibody, multi-specific antibody, or chimeric antibody.

The anti-Siglec-10 antibody may comprise one or more sequences of antibody 31F11, which comprises heavy and light chain variable regions comprising the sequences set forth in SEQ ID NOS: 1 and 2, respectively. The antibody may comprise a heavy chain variable region comprising the sequence set forth in SEQ ID NO: 1, and may comprise a light chain variable region comprising the sequence set forth in SEQ ID NO: 2. The heavy chain variable region of the anti-Siglec-10 antibody may comprise one or more of: a CDR1 comprising the sequence set forth in SEQ ID NO: 3, a CDR2 comprising the sequence set forth in SEQ ID NO: 4, and a CDR3 comprising the sequence set forth in SEQ ID NO: 5. The light chain variable region of the anti-Siglec-10 antibody may comprise one more of: a CDR1 comprising the sequence set forth in SEQ ID NO: 6, a CDR2 comprising the sequence set forth in SEQ ID NO: 7, and a CDR3 comprising the sequence set forth in SEQ ID NO: 8. In one example, the antibody is a chimeric antibody comprising the variable domains of 31F11 attached to a human Fc domain.

In one embodiment, the heavy chain variable region comprises CDR1-3 having SEQ ID NOS: 3-5, respectively. In another embodiment, the light chain variable region comprises CDR1-3 having SEQ ID NOS: 6-8, respectively. In a further example, the anti-Siglec-10 antibody comprises the heavy chain variable region comprising SEQ ID NOS: 3-5 and the light chain variable region comprising SEQ ID NOS: 6-8.

One or more of the heavy and light chains of the anti-Siglec-10 antibody may also be humanized relative to 31F111. The anti-Siglec-10 antibody may comprise one or more heavy chain variable regions, each comprising the sequence set forth in one of SEQ ID NOS: 9, 10, 11, 12, and 13 (named Hu-VHv1, VHv2, VHv3, VHv4, and VHv5, respectively). The anti-Siglec-10 antibody may comprise one or more light chain variable regions, each comprising the sequence set forth in one of SEQ ID NOS: 14-18 (named Hu-VLv1, VLv2, VLv3, VLv4, and VLv5, respectively).

The sequences of heavy and light chain variable regions of 31F11 are provided below.

```
31F11 heavy chain variable region
                                          (SEQ ID NO: 1)
QVTLKESGPGILQSSQTLSLTCSFSGFSLSTSGMGLSWIRQPSGK

GLEWLAHIYWDDDKRYNPSLKSRLTISKDTSRNQVFLKITSVDTA

DTATYYCVRGLYGNWFFDVWGAGTTVTVSS
```

-continued

31F11 light chain variable region
(SEQ ID NO: 2)
DIVMTQSQKFMSTSVGDRVSITYKASQNVGTAVAWYQQKPGQSPK
LLIYSASNRYTGVPDRFTGSGSGTDFTLTISNMQSENLANYFCQQ
YSSYPLTFGAGTKLELK Sequences of the humanized 31F11 heavy chain variable regions are provided below (CDRs underlined).

Hu-31F11-VHv1
(SEQ ID NO: 9)
QVTLKESGPalvkptQTLtLTCtFSGFSLSTSGMGLSWIRQPpGK
aLEWLAHIYWDDDKRYNPSLKSRLTISKDTSKNQVvLtmTnmDpv
DTATYYCVRGLYGNWFFDVWGqGTTVTVSS Hu-31F11-VHv2
(SEQ ID NO: 10)
QVTLKESGPalvkptQTLtLTCtFSGFSLSTSGMGLSWIRQPpGK
aLEWLAHIYWDDDKRYNPSLKSRLTISKDTSKNQVvLtmTnmDpv
DTATYYCVRGLYGNWFFDVWGAGTTVTVSS Hu-31F11-VHv3
(SEQ ID NO: 11)
QVTLKESGPalvkptQTLtLTCtFSGFSLSTSGMGLSWIRQPpGK
aLEWLAHIYWDDDKRYNPSLKSRLTISKDTSKNQVvLtmTnmDpv
DTATYYCaRGLYGNWFFDVWGqGTTVTVSS Hu-31F11-VHv4
(SEQ ID NO: 12)
QVTLKESGPalvkptQTLtLTCtFSGFSLSTSGMGLSWIRQPpGK
aLEWLAHIYWDDDKRYNPSLKSRLTISKDTSKNQVvLtmTnmDpv
DTATYYCaRGLYGNWFFDVWGAGTTVTVSS Hu-31F11-VHv5
(SEQ ID NO: 13)
QVTLKESGPalvkptQTLtLTCtFSGFSLSTSGMGLSWIRQPpGK
aLEWLAHIYWDDDKRYNPSLKSRLTISKDTSKNQVvLtmTnmDpv
DTATYYCaRGLYGNWFFDVWGqGTIVTVSS Sequences of the humanized 31F11 light chain variable regions are provided below (CDRs underlined).

Hu 31F11-VLv1
(SEQ ID NO: 14)
eIVMTQSpatlSvSpGeRatlscKASQNVGTAVAWYQQKPGQaPI
LLIYSASNRYTGVPaRFsGSGSGTEFTLTISslQSEdfAvYyCQ
QYSSYPLTFGgGTKVEIK Hu 31F11-VLv2
(SEQ ID NO: 15)
DIVMTQSpatlSvSpGeRatlscKASQNVGTAVAWYQQKPGQaPr
LLIYSASNRYTGVPaRFsGSGSGTEFTLTISslQSEdfAvYFCQ
QYSSYPLTFGgGTKVEIK Hu 31F11-VLv2-full light chain
(SEQ ID NO: 27)
DIVMTQSPATLSVSPGERATLSCKASQNVGTAVAWYQQKPGQAPR
LLIYSASNRYTGVPARFSGSGSGTEFTLTISSLQSEDFAVYFCQ
QYSSYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC Hu 31F11-VLv2-full light chain plus signal peptide
(SEQ ID NO: 28)
METDTLLLWVLLLWVPGSTGDIVMTQSPATLSVSPGERATLSCKA
SQNVGTAVAWYQQKPGQAPRLLIYSASNRYTGVPARFSGSGSGT
EFTLTISSLQSEDFAVYFCQQYSSYPLTFGGGTKVEIKRTVAAPS
VFIFPPSDEQLKSGTASVVCLLNNFYPREAKVQWKVDNALQSGNS
QESVTEQDSKDSTYSLSSTLTLSKADYEKHKVYACEVTHQGLSSP
VTKSFNRGEC Hu 31F11-VLv3
(SEQ ID NO: 16)
eIVMTQSpatlSvSpGeRatlsYKASQNVGTAVAWYQQKPGQaPr
LLIYSASNRYTGVPaRFsGSGSGTEFTLTISslQSEdfAvYyCQ
QYSSYPLTFGgGTKVEIK Hu 31F11-VLv3-full light chain
(SEQ ID NO: 34)
EIVMTQSPATLSVSPGERATLSYKASQNVGTAVAWYQQKPGQAPR
LLIYSASNRYTGVPARFSGSGSGTEFTLTISSLQSEDFAVYYCQ
QYSSYPLTFGGGTKVEIKRTVAAPSVFIFPPSDEQLKSGTASVVC
LLNNFYPREAKVQWKVDNALQSGNSQESVTEQDSKDSTYSLSSTL
TLSKADYEKHKVYACEVTHQGLSSPVTKSFNRGEC Hu 31F11-VLv3-full light chain plus signal peptide
(SEQ ID NO: 35)
METDTLLLWVLLLWVPGSTGEIVMTQSPATLSVSPGERATLSYKA
SQNVGTAVAWYQQKPGQAPRLLIYSASNRYTGVPARFSGSGSGT
EFTLTISSLQSEDFAVYYCQQYSSYPLTFGGGTKVEIKRTVAAPS
VFIFPPSDEQLKSGTASVVCLLNNFYPREAKVQWKVDNALQSGNS
QESVTEQDSKDSTYSLSSTLTLSKADYEKHKVYACEVTHQGLSSP
VTKSFNRGEC Hu 31F11-VLv4
(SEQ ID NO: 17)
DIVMTQSpatlSvSpGeRatlsYKASQNVGTAVAWYQQKPGQaPr
LLIYSASNRYTGVPaRFsGSGSGTEFTLTISslQSEdfAvYFCQ
QYSSYPLTFGgGTKVEIK Hu 31F11-VLv5
(SEQ ID NO: 18)
DIVMTQSpatlSvSpGeRatITYKASQNVGTAVAWYQQKPGQaPr
LLIYSASNRYTGVPaRFsGSGSGTEFTLTISslQSEdfAvYFCQ
QYSSYPLTFGgGTKVEIK In one example, the anti-Siglec-10 antibody comprises the heavy chain variable region comprising the sequence set forth in SEQ ID NO: 9 or the heavy chain comprising the sequence set forth in SEQ ID NO: 25, and the light chain variable region comprising the sequence set forth in SEQ ID NO: 15 or the light chain comprising the sequence set forth in SEQ ID NO: 27. The anti-Siglec-10 antibody may comprise hu-VHv1VLv2.

In another example, the anti-Siglec-10 antibody comprises the heavy chain variable region comprising the sequence set forth in SEQ ID NO: 10 or the heavy chain comprising the sequence set forth in SEQ ID NO: 32, and the light chain variable region comprising the sequence set forth in SEQ ID NO: 15 or the light chain comprising the sequence set forth in SEQ ID NO: 27. The anti-Siglec-10 antibody may comprise hu-VHv2VLv2.

In a further example, the anti-Siglec-10 antibody comprises the heavy chain variable region comprising the sequence set forth in SEQ ID NO: 10 or the heavy chain comprising the sequence set forth in SEQ ID NO: 32, and the light chain variable region comprising the sequence set forth in SEQ ID NO: 16 or the light chain comprising the sequence set forth in SEQ ID NO: 34. The anti-Siglec-10 antibody may comprise hu-VHv2VLv3.

The anti-Siglec-10 antibody may comprise the heavy chain variable region comprising the sequence set forth in SEQ ID NO: 9, 10, or 11; and the light chain variable region comprising the sequence set forth in SEQ ID NO: 15, 27, 16 or 34.

In another example, the anti-Siglec-10 antibody comprises the heavy chain variable region comprising the sequence set forth in SEQ ID NO: 10 and the light chain variable region comprising the sequence set forth in SEQ ID NO: 17. The anti-Siglec-10 antibody may comprise hu-VHv2VLv4. In a further example, the anti-Siglec-10 antibody comprises the heavy chain variable region comprising the sequence set forth in SEQ ID NO: 12 and the light chain variable region comprising the sequence set forth in SEQ ID NO: 17. The anti-Siglec-10 antibody may comprise hu-VHv4VLv4. The anti-Siglec-10 antibody may comprise the heavy chain variable region comprising the sequence set forth in SEQ ID NO: 10 or 12; and the light chain variable region comprising the sequence set forth in SEQ ID NO: 17.

In another example, the anti-Siglec-10 antibody comprises the heavy chain variable region comprising the sequence set forth in SEQ ID NO: 12 and the light chain variable region comprising the sequence set forth in SEQ ID NO: 16 or 34. The anti-Siglec-10 antibody may comprise hu-VHv4VLv3.

In another example, the anti-Siglec-10 antibody comprises the heavy chain variable region comprising the sequence set forth in SEQ ID NO: 10; and the light chain variable region comprising the sequence set forth in SEQ ID NO: 15 or 17. In a further example, the anti-Siglec-10 antibody comprises the heavy chain variable region comprising the sequence set forth in SEQ ID NO: 12; and the light chain variable region comprises the sequence set forth in SEQ ID NO: 16, 34, or 17.

The anti-Siglec-10 antibody may comprise a human Igκ polypeptide. In one example, the Igκ has the sequence set forth in SEQ ID NO: 19. The anti-Siglec-10 antibody may comprise a human IgG polypeptide, which may be IgG1, IgG2, IgG3, IgG4, IgA1, or IgA2. In one example, the IgG is IgG4, which may have the sequence set forth in SEQ ID NO: 20. In another example, the IgG4 may include a S228P mutation, which may have the following sequence.

(SEQ ID NO: 24)

```
ASTKGPSVFPLAPCSRSTSESTAALGCLVKDYFPEPVTVSWNSGA
LTSGVHTFPAVLQSSGLYSLSSVVTVPSSSLGTKTYTCNVDHKP
SNTKVDKRVESKYGPPCPPCPAPEFLGGPSVFLFPPKPKDTLMIS
RTPEVTCVVVDVSQEDPEVQFNWYVDGVEVHNAKTKPREEQFNST
YRVVSVLTVLHQDWLNGKEYKCKVSNKGLPSSIEKTISKAKGQPR
```

-continued

```
EPQVYTLPPSQEEMTKNQVSLTCLVKGFYPSDIAVEWESNGQPEN
NYKTTPPVLDSDGSFFLYSRLTVDKSRWQEGNVFSCSVMHEALHN
HYTQKSLSLSLGK
```

In another example, the anti-Siglec-10 antibody comprises a heavy chain variable region comprising the sequence set forth in SEQ ID NO: 9 and the S228P mutant IgG4 comprising the sequence set forth in SEQ ID NO: 24. The heavy chain (VHv1) may comprise the sequence set forth below.

(SEQ ID NO: 25)

```
QVTLKESGPALVKPTQTLTLTCTFSGFSLSTSGMGLSWIRQPPGK
ALEWLAHIYWDDDKRYNPSLKSRLTISKDTSKNQVVLTMTNMDP
VDTATYYCVRGLYGNWFFDVWGQGTTVTVSSASTKGPSVFPLAPC
SRSTSESTAALGCLVKDYFPEPVTVSWNSGALTSGVHTFPAVLQS
SGLYSLSSVVTVPSSSLGTKTYTCNVDHKPSNTKVDKRVESKYGP
PCPPCPAPEFLGGPSVFLFPPKPKDTLMISRTPEVTCVVVDVSQE
DPEVQFNWYVDGVEVHNAKTKPREEQFNSTYRVVSVLTVLHQDWL
NGKEYKCKVSNKGLPSSIEKTISKAKGQPREPQVYTLPPSQEEMT
KNQVSLTCLVKGFYPSDIAVEWESNGQPENNYKTTPPVLDSDGSF
FLYSRLTVDKSRWQEGNVFSCSVMHEALHNHYTQKSLSLSLGK
```

The heavy chain (VHv1) having the sequence set forth in SEQ ID NO: 25 may further comprise a signal peptide, and may have the sequence set forth below.

(SEQ ID NO: 26)

```
MGWSCIILFLVATATGVHSQVTLKESGPALVKPTQTLTLTCTFSG
FSLSTSGMGLSWIRQPPGKALEWLAHIYWDDDKRYNPSLKSRLT
ISKDTSKNQVVLTMTNMDPVDTATYYCVRGLYGNWFFDVWGQGTT
VTVSSASTKGPSVFPLAPCSRSTSESTAALGCLVKDYFPEPVTVS
WNSGALTSGVHTFPAVLQSSGLYSLSSVVTVPSSSLGTKTYTCNV
DHKPSNTKVDKRVESKYGPPCPPCPAPEFLGGPSVFLFPPKPKDT
LMISRTPEVTCVVVDVSQEDPEVQFNWYVDGVEVHNAKTKPREEQ
FNSTYRVVSVLTVLHQDWLNGKEYKCKVSNKGLPSSIEKTISKAK
GQPREPQVYTLPPSQEEMTKNQVSLTCLVKGFYPSDIAVEWESNG
QPENNYKTTPPVLDSDGSFFLYSRLTVDKSRWQEGNVFSCSVMHE
ALHNHYTQKSLSLSLGK
```

The heavy chain (VHv2) may comprise the following sequence:

(SEQ ID NO: 32)

```
QVTLKESGPALVKPTQTLTLTCTFSGFSLSTSGMGLSWIRQPPGK
ALEWLAHIYWDDDKRYNPSLKSRLTISKDTSKNQVVLTMTNMDP
VDTATYYCVRGLYGNWFFDVWGAGTTVTVSSASTKGPSVFPLAPC
SRSTSESTAALGCLVKDYFPEPVTVSWNSGALTSGVHTFPAVLQS
```

-continued

```
SGLYSLSSVVTVPSSSLGTKTYTCNVDHKPSNTKVDKRVESKYGP

PCPPCPAPEFLGGPSVFLFPPKPKDTLMISRTPEVTCVVVDVSQE

DPEVQFNWYVDGVEVHNAKTKPREEQFNSTYRVVSVLTVLHQDWL

NGKEYKCKVSNKGLPSSIEKTISKAKGQPREPQVYTLPPSQEEMT

KNQVSLTCLVKGFYPSDIAVEWESNGQPENNYKTTPPVLDSDGSF

FLYSRLTVDKSRWQEGNVFSCSVMHEALHNHYTQKSLSLSLGK
```

The heavy chain (VHv2) may also comprise the following sequence:

```
                                  (SEQ ID NO: 33)
MGWSCIILFLVATATGVHSQVTLKESGPALVKPTQTLTLTCTFSG

FSLSTSGMGLSWIRQPPGKALEWLAHIYWDDDKRYNPSLKSRLT

ISKDTSKNQVVLTMTNMDPVDTATYYCVRGLYGNWFFDVWGAGTT

VTVSSASTKGPSVFPLAPCSRSTSESTAALGCLVKDYFPEPVTVS

WNSGALTSGVHTFPAVLQSSGLYSLSSVVTVPSSSLGTKTYTCNV

DHKPSNTKVDKRVESKYGPPCPPCPAPEFLGGPSVFLFPPKPKDT

LMISRTPEVTCVVVDVSQEDPEVQFNWYVDGVEVHNAKTKPREEQ

FNSTYRVVSVLTVLHQDWLNGKEYKCKVSNKGLPSSIEKTISKAK

GQPREPQVYTLPPSQEEMTKNQVSLTCLVKGFYPSDIAVEWESNG

QPENNYKTTPPVLDSDGSFFLYSRLTVDKSRWQEGNVFSCSVMHE

ALHNHYTQKSLSLSLGK
```

The anti-Siglec-10 antibody may comprise the heavy chain comprising the sequence set forth in SEQ ID NO: 9 or 25, and the light chain comprising the sequence set forth in SEQ ID NO: 15 or 27 (VHv1VLv2). In one example, the anti-Siglec-10 antibody may comprise the heavy chain comprising the sequence set forth in SEQ ID NO: 25 and the light chain comprising the sequence set forth in SEQ ID NO: 27. The anti-Siglec-10 antibody may comprise the heavy chain comprising the sequence set forth in SEQ ID NO: 10 or 32, and the light chain comprising the sequence set forth in SEQ ID NO: 15 or 27 (VHv2VLv2). In one example, the antibody comprises the heavy chain comprising the sequence set forth in SEQ ID NO: 32 and the light chain comprising the sequence set forth in SEQ ID NO: 27. The anti-Siglec-10 antibody may comprise the heavy chain comprising the sequence set forth in SEQ ID NO: 10 or 32, and the light chain comprising the sequence set forth in SEQ ID NO: 16 or 34 (VHv2VLv3). In one example, the antibody comprises the heavy chain comprising the sequence set forth in SEQ ID NO: 32 and the light chain comprising the sequence set forth in SEQ ID NO: 34.

3. Bi-Specific Antibody Compositions

Also provided herein is a bi-specific antibody comprising the antibody that binds to Siglec-10, bridged to an antibody that binds other immune-stimulating, immune cell targeting or cancer-targeting molecules. In a specific embodiment, the bi-specific antibody comprises the anti-Siglec-10 antibody or antigen binding fragment thereof, and a cancer-targeting antibody or antigen binding fragment thereof. Such a molecule would be enriched in the tumor microenvironment. The cancer-targeting antibody include may be specific T-antigen, TN-antigen, differentially glycosylated mucin, CD24, her-2, or PMSA.

In another embodiment, the anti-Siglec-10 bi-specific antibody may comprise a second antibody, or antigen binding fragment thereof, that targets a complementary anti-tumor pathway or mechanism. In one embodiment, the anti-Siglec-10 antibody compositions described herein may be combined with a cancer immunotherapy antibody that amplifies natural immune responses. Examples of such cancer immunotherapy antibodies include anti-PD-1, anti-CTLA-4, anti-PD-L1, anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-CD47, anti-ICOS or anti-4-1BB. Such antibodies may be used to treat of cancer.

There are many different bi-specific antibody technologies known in the art. Most of these require that the two-component antibodies are in a single chain format so that the two parts can be expressed in a single construct. A preferred method is to express the antibodies as a single-chain variable fragment (scFv). Non-limiting examples of bi-specific antibody technologies include BiTE (for Bi-specific T-cell Engager), DART (for Dual-Affinity Re-Targeting), Fabs-in-tandem immunoglobulin (FIT-Ig), and knobs-into-holes.

Methods of Treatment

Provided herein are uses of the antibody compositions described herein, and pharmaceutical compositions thereof, for treating cancer. As used herein, the term "cancer" refers to a neoplasm or tumor resulting from abnormal uncontrolled growth of cells. As used herein, cancer explicitly includes leukemia and lymphomas. The term refers to a disease involving cells that have the potential to metastasize to distal sites.

Provided herein is a method of treating a cancer or abnormal proliferative disease in a subject in need thereof, which may comprise administering the antibody composition to the subject. The subject may be a mammal, such as a dog, cat, pig, horse, cow, monkey, ape, or human. In one example, the subject is a human patient. Also provided is a pharmaceutical composition comprising the antibody composition for use in treating the cancer or abnormal proliferative disease. Further provided is use of the antibody composition in the manufacture of a medicament for treating the cancer or abnormal proliferative disease. In one example, the antibody composition is used as monotherapy, which may facilitate phagocytosis of cancer cells by one or more of macrophages, ADCC, and antibody-dependent cellular phagocytosis (ADCP).

The cancer may be one or more of (but is not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderoma pigmentosum, keratoacanthoma, seminoma, thyroid follicular cancer, and teratocarcinoma. In particular, the cancer may be breast cancer, triple-negative breast cancer, ovarian cancer, or a leukemia disclosed herein. The cancer may include infiltrating cells that bind to the anti-Siglec-10 antibody.

The cancer may be an advanced solid tumor. The advanced solid tumor may have progressed after standard of care systemic therapy. The cancer may be a lung adenocarcinoma (LUAD), a skin cutaneous melanoma-metastasis (SKCM-TM), a lung squamous cell carcinoma (LUSC), a breast invasive carcinoma—basal, a breast invasive carcinoma—Her2, a pancreatic adenocarcinoma, a head and neck squamous cell carcinoma, a kidney renal clear cell carcinoma, a stomach adenocarcinoma, a glioblastoma multiforme, a breast invasive carcinoma—LumB, or a breast invasive carcinoma—LumA, a non-small cell lung cancer, a glioblastoma, a melanoma, a low grade glioma, a kidney cancer, a breast cancer basal type, a Her2+ breast cancer, a pancreatic cancer, or an ovarian cancer. In one example, the cancer is a LUAD, a SKCM-TM, or a LUSC. In particular, the cancer may be a non-small cell lung adenocarcinoma. The cancer may also be a hematological malignancy, which may be a leukemia, a myeloid dysplasia syndrome, a B cell lymphoma, or a multiple myeloma.

The cancer may be caused by aberrations in apoptosis, and may also be treated by the methods and compositions described herein. The cancer may be one or more of (but is not limited to): a follicular lymphoma, carcinoma with p53 mutations, hormone-dependent tumor of the breast, prostate or ovary, and a precancerous lesion such as familial adenomatous polyposis or a myelodysplastic syndrome. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, one or more of sarcoma, melanoma, and leukemia is treated or prevented by the methods and compositions described herein.

In another embodiment, the antibody composition is used in combination with one or more other anti-tumor therapies, including but not limited to, current standard and experimental chemotherapies, hormonal therapies, biological therapies, immunotherapies, radiation therapies, or surgery. In some embodiments, the antibody composition is administered in combination with a therapeutically or prophylactically effective amount of one or more agents, therapeutic antibodies or other agents known to those skilled in the art for the treatment and/or prevention of cancer, autoimmune disease, infectious disease or intoxication. Such agents include for example, any of the above-discussed biological response modifiers, cytotoxins, antimetabolites, alkylating agents, antibiotics, or anti-mitotic agents, as well as immunotherapeutics.

In preferred embodiment of the invention, the antibody composition is used with one or more anti-tumor immunotherapies. The anti-tumor immunotherapy may be a molecule that disrupts or enhances one or more alternative immunomodulatory pathways (such as TIM3, TIM4, OX40, CD40, GITR, 4-1-BB, PD-L1, PD-1, B7-H3, B7-H4, CTLA-4, LIGHT, BTLA, ICOS, CD27, CD47, TIGIT or LAG3), or modulates the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. In yet another embodiment, the antibody composition is administered in combination with one or more molecules that activate different stages or aspects of the immune response in order to achieve a broader immune response. In more preferred embodiment, the antibody composition is combined with anti-PD-1 or anti-4-1BB antibodies, without exacerbating autoimmune side effects.

The antibody composition may be used with a tumor-targeting antibody. The tumor-targeting antibody may any that causes one or more of ADCC or ADCP. The tumor-targeting antibody may be cetuximab (Erbitux), rituximab (Rituxan), trastuzumab (Herceptin), or daratumumab (Darzalex). The antibody composition may also be used with a host-cell-targeting immunotherapeutic, which may be an anti-CTLA-4 antibody. Anti-CTLA-4 antibodies are known in the art. The anti-CTLA-4 antibody may be disclosed in U.S. Pat. No. 10,618,960, the contents of which are incorporated herein by reference. In one example, the anti-CTLA-4 antibody has a heavy chain variable region comprising SEQ ID NO: 21 and a light chain variable region comprising SEQ ID NO: 22. The anti-CTLA-4 antibody light chain may further comprise a constant region comprising SEQ ID NO: 29, and the heavy chain may further comprise a constant region comprising SEQ ID NO: 30 or 31. In another example, the anti-CTLA-4 antibody has a heavy chain comprising a variable region comprising SEQ ID NO: 21 and a constant region comprising SEQ ID NO: 31; and a light chain comprising a variable region comprising SEQ ID NO: 22 and a constant region comprising SEQ ID NO: 29.

Production

The anti-Siglec-10 antibodies described herein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The antibodies may also be produced from a stable cell line that expresses the antibody from a vector or a portion of a vector that has been integrated into the cellular genome. The stable cell line may express the antibody from an integrated replication-defective retroviral vector.

The anti-Siglec-10 antibody described herein or antigen binding fragment thereof can be purified using, for example, chromatographic methods such as affinity chromatography, ion exchange chromatography, hydrophobic interaction chromatography, DEAE ion exchange, gel filtration, and hydroxylapatite chromatography. In some embodiments, fusion proteins can be engineered to contain an additional domain containing amino acid sequence that allows the polypeptides to be captured onto an affinity matrix. For example, the antibodies described herein comprising the Fc region of an immunoglobulin domain can be isolated from cell culture supernatant or a cytoplasmic extract using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides.

Pharmaceutical Compositions

Provided herein is a pharmaceutical composition comprising a therapeutically effective amount of one or more of the anti-Siglec-10 antibodies and compositions described herein, and a physiologically acceptable carrier or excipient. The pharmaceutical composition may comprise a prophylactically or therapeutically effective amount of the anti-Siglec-10 antibody and a pharmaceutically acceptable carrier In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, may also contain minor amounts of wetting or emulsifying agents, or pH buffering agents. These compositions may take the form of solutions, suspensions, emulsion, tablets, pills, capsules, powders, sustained-release formulations and the like.

Generally, the ingredients of the pharmaceutical composition may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline may be provided so that the ingredients may be mixed prior to administration.

The pharmaceutical composition may be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The pharmaceutical composition may comprise one or more, or all of, histidine buffer, sucrose, and polysorbate 80 (PS80). In one example, the pharmaceutical composition comprises about 15, 16, 17, 18, 19, 20, 21, 22, 23, 24, or 25 mM histidine buffer. In particular, the histidine buffer concentration may be 20 mM. The pharmaceutical composition may comprise about 6, 7, 8, 9, or 10% w/v sucrose. In one example, the pharmaceutical composition comprises 8% sucrose. The pharmaceutical composition may comprise about 0.01, 0.02, or 0.03% PS80. In one example, the PS80 concentration is 0.02%. In one example, the pharmaceutical composition comprises 20 mM histidine buffer, 8% sucrose, and 0.02% w/v PS80. The pharmaceutical composition may have a pH of about 5, 5.5, or 6.0. In one example, the pH is 5.5. The pharmaceutical composition may be diluted in 0.9% sodium chloride or 5% dextrose solution before being administered to a subject.

The anti-Siglec-10 antibody, which may be ONC-841, may be present in the pharmaceutical composition at about 10, 15, 20, 25, or 30 mg/mL. The anti-Siglec-10 antibody may be administered at a dose of about 1, 2, 3, 4 5, 6, 7, 8, or 9 mg/kg. The dose may be less than 10 mg/kg. In one example, the dose is 3-9 mg/kg. In another example, the dose is 3 mg/kg. A subsequent dose may be adjusted downwards from a previous dose if the subject suffers adverse events associated with administration of the antibody composition. A subsequent dose may be adjusted upwards from a previous dose if the antibody composition is not having a sufficiently strong effect against a cancer.

Methods of Administration

Methods of administering the anti-Siglec-10 antibody compositions and the pharmaceutical compositions thereof described herein include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

EXAMPLES

The disclosure has multiple aspects, illustrated by the following non-limiting examples.

Example 1

Generation of Monoclonal Anti-Siglec-10 Antibodies

Figure 1:
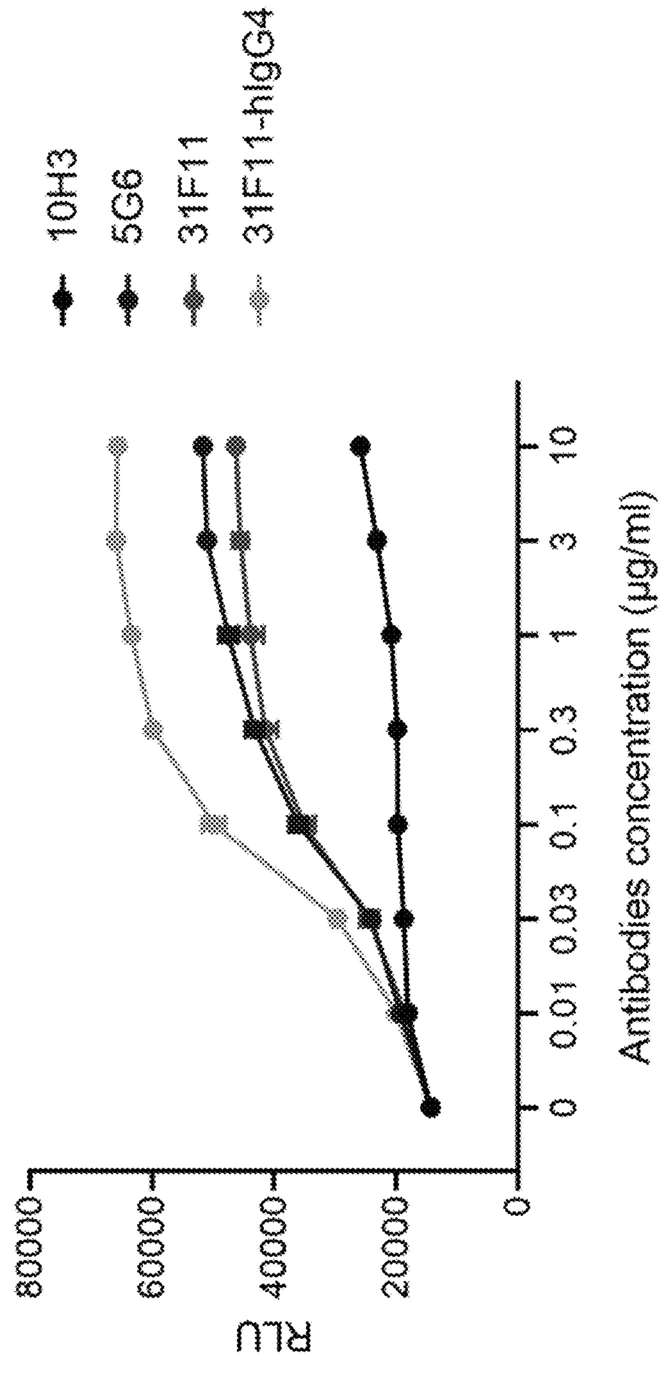
FIG. 1 shows the antagonist activity of anti-Siglec-10 antibodies in a reporter assay for antibody-dependent cell-mediated cytotoxicity (ADCC). Grading doses of 4 different anti-Siglec-10 antibodies were compared for their ability to rescue ADCC suppressed by Siglec-10 ectopically expressed in Jurkat ADCC effector cells. Target: CHO-CTLA4-OFP clone 9 (2x10e4). Effector: Jurkat-PWPI-Siglec10 ($2\times10^4$). ADCC-triggering antibody: anti-CTLA4 mAb (0.1 μg/ml).

To generate an antagonist, mice were immunized with Siglec-10-transfected murine cell lines, after three immunizations, spleen cells were harvested for generation of hybridoma. The hybridoma supernatants were screened for their activity in reversing the inhibitory effect of Siglec-10 in ADCC, which was measured using effector cells expressing human FcγRIIIa. Out of more than 20,000 clones, one (31F11) was found to be most potent in reversing the inhibition by Siglec-10 (FIG. 1). Compared with another anti-Siglec-10 antibodies (10H3 and 5G6), 31F11 is more potent in antagonizing the Siglec-10 function.

Figure 2:
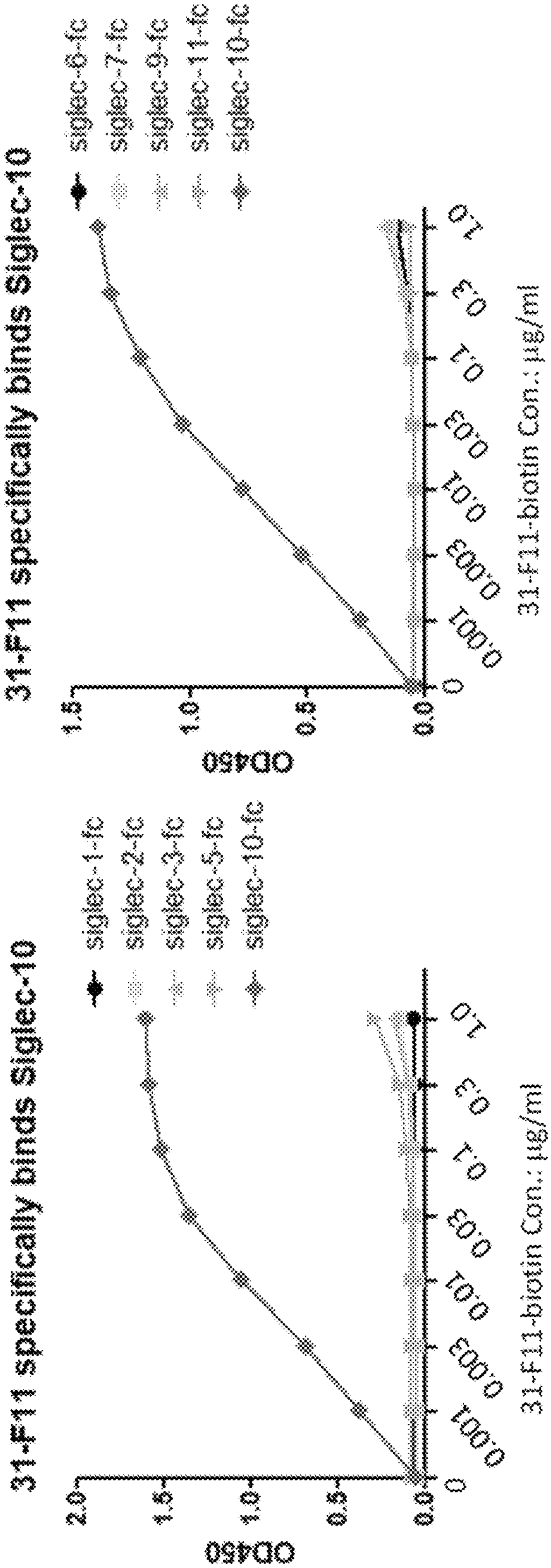
FIG. 2 shows the binding specificity of anti-Siglec-10 mAb 31F11 as determined by ELISA. Siglec fusion proteins were coated on the plate, and the biotinylated 31F11 was added. The bound antibody was detected by horse radish peroxidases-conjugated Streptavidin.
Figure 3:
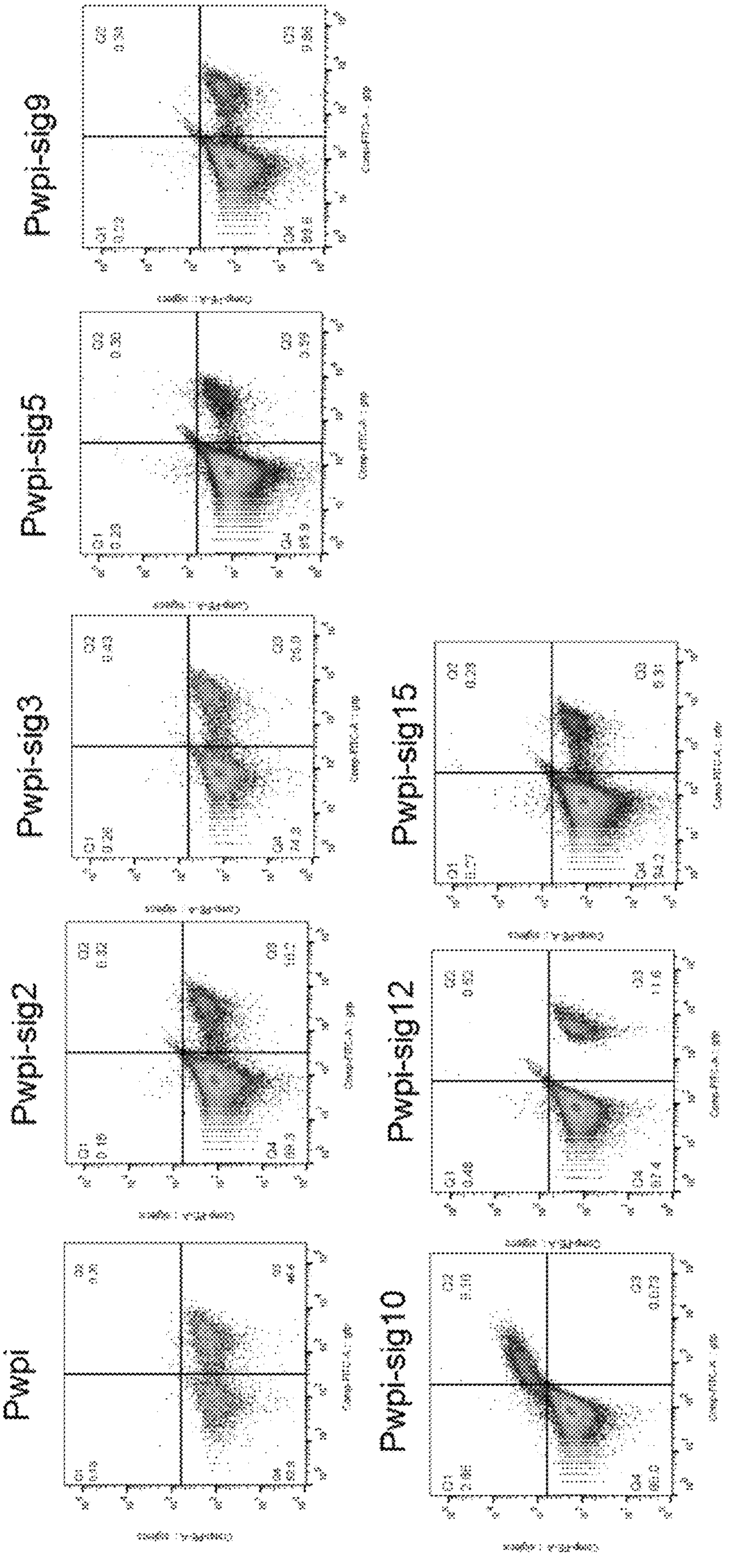
FIG. 3 shows the binding specificity of anti-Siglec-10 mAb 31F11 as determined by flow cytometry. 293T cells were transfected with GFP-conjugated Siglec cDNAs. The cells were stained with 31F11 and analyzed by Canto II cytometer.

To confirm the specificity of 31F11, we coated plates with fusion proteins consisting of the extracellular domains of Siglecs 1, 2, 3, 5, 6, 7, 9, 10, and, 11 and tested the binding of 3F11 to these Siglecs. As shown in FIG. 2, only Siglec-10 showed appreciable binding to 31F11. As an alternative approach, we transfected 293T cell line with GFP-tagged Siglecs 2, 3, 5, 9, 10, 12, and 15. As shown in FIG. 3, 31F11 binds specifically to cells expressing Siglec-10, but not any other Siglecs tested. Taken together, data in FIGS. 2 and 3 demonstrate that 31F11 binds to Siglec-10, but not Siglecs 1, 2, 3, 5, 6, 7, 9, 11, 12 and 15.

Example 2

Anti-Siglec10 Antibodies Block Siglec-10-Fc Binding to Splenocytes

Figure 4A:
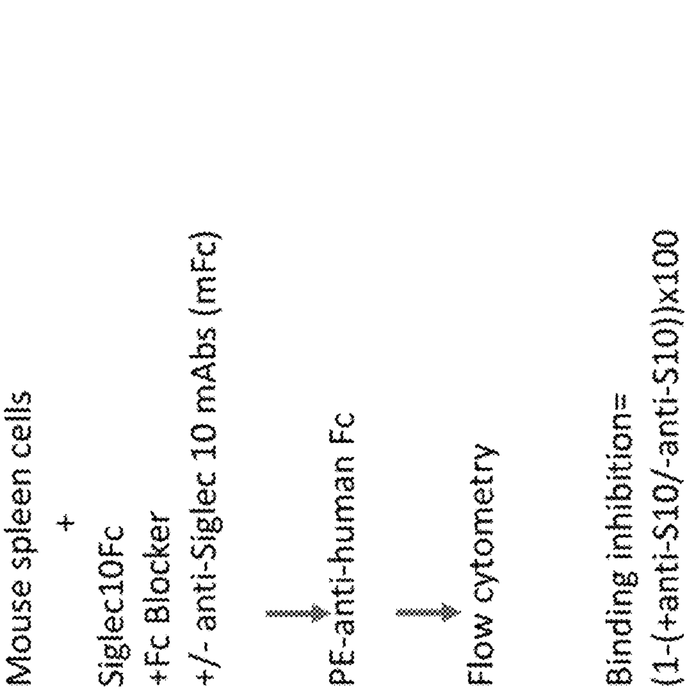
FIGS. 4A-B show that anti-Siglec-10 mAb 31F11 exhibits potent inhibition for Siglec-10Fc binding to mouse spleen cells.
Figure 4B:
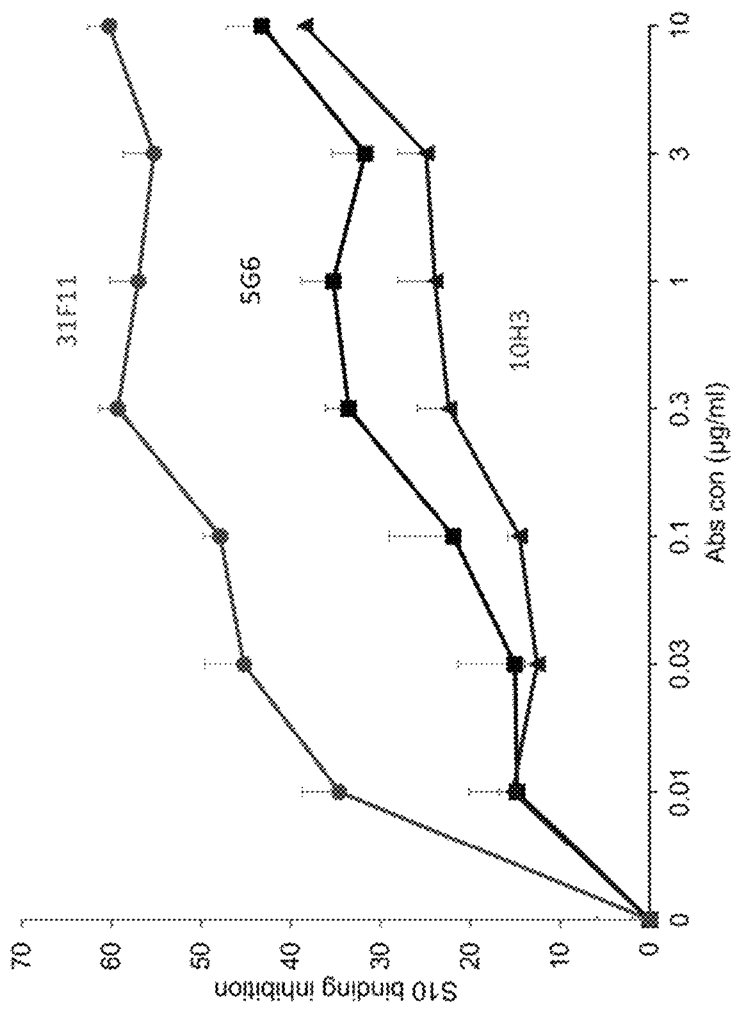

To confirm if 31F11 blocks Siglec-10 binding to its ligands, we tested the effect of 31F11 on Siglec-10-Fc binding to mouse spleen cells. As shown in FIG. 4, 31F11 is more potent than other anti-Siglec-10 antibodies (5G6 and 10H3) in blocking Siglec-10-Fc binding to spleen cells.

Example 3

Anti-Siglec-10 Antibodies Phagocytosis Assay

Figure 5:
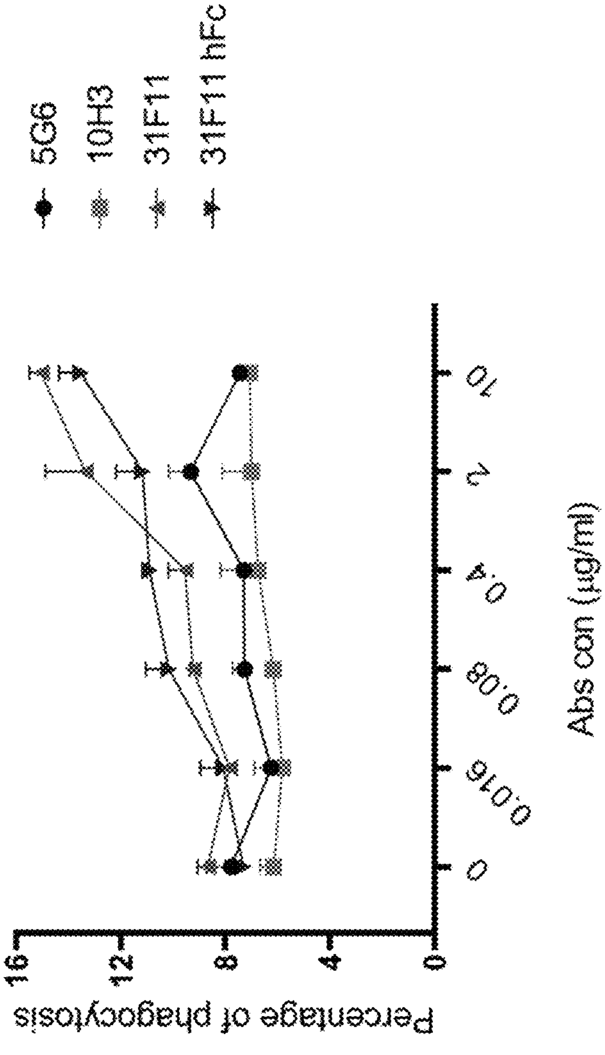
FIG. 5 shows that anti-Siglec-10 mAb 31F11 promotes phagocytosis of cancer cells by macrophages. Human monocytes isolated from peripheral blood were stimulated with RPMI-1640 medium supplemented with 40 ng/ml M-CSF for 5-7 days. Then M2 macrophage were induced by 50 ng/ml TGFβ1 and IL10 for 24 h. MCF-7 cells were labeled with CELLTRACE™ Violet BMQC Dye and cocultured with donor-derived M2 macrophages in the presence of an anti-siglec-10 mAbs, 5G6, 10H3 and 31F11 (mFc=murine Fc; hFc=human Fc), of indicated concentration for 2 hours. The cells were stained with APC-conjugated anti-CD1 lb Ab and phagocytosis (%) was determined by flow cytometry based on % of Violet dye positive CD11b+ cells among total CD11b+ cells. Data shown are means and standard errors of % macrophages that have engulfed cancer cells, as determined by flow cytometry.

To test if anti-Siglec-10 promotes phagocytosis of cancer cells by macrophages, human monocytes isolated from peripheral blood were stimulated with RPMI-1640 medium supplemented with 40 ng/ml M-CSF for 5-7 days. Then M2 macrophages were induced by 50 ng/ml TGFβ1 and IL10 for 24 h. MCF-7 cells were labeled with CellTracker™ Violet BMQC Dye and cocultured with donor-derived macrophages in the presence of anti-Siglec-10 Abs of indicated concentration for 2 hours. The % of macrophages undergoing phagocytosis was determined by flow cytometry. As shown in FIG. 5, 31F11 more than doubled phagocytosis, while other anti-Siglec-10 antibodies have no appreciable effect. Thus, 31F11 is unique is promoting phagocytosis.

Example 4

Anti-Tumor Activity Combined with Anti-hCD24 Antibodies

Figure 6A:
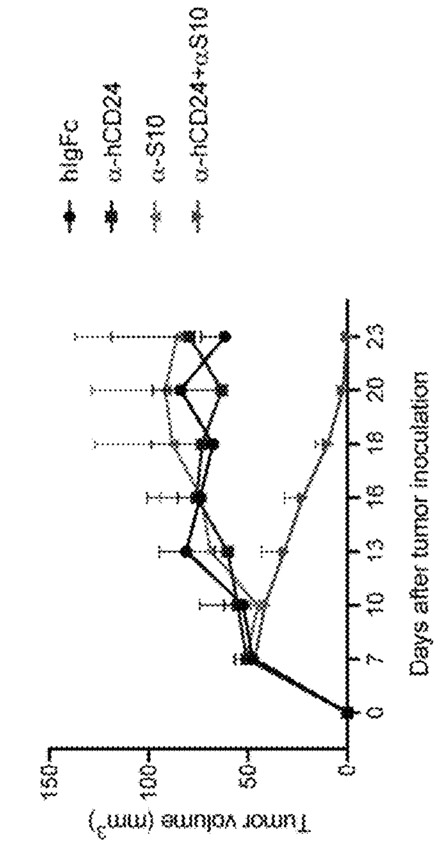
FIGS. 6A-B show synergistic anti-tumor activity of anti-CD24 and anti-Siglec-10 antibodies. $1\times10^6$ MC38-hCD24 cell were inoculated subcutaneously to BM Chimeric mice consisting of bone marrow cells from transgenic mice expressing human Siglec-10 (n-4-5). Mice were treated with 100 μg hIgFc, α-hCD24, 31F11 (α-S10) or α-hCD24+31F11 Abs on days 7, 10, 13 and 16 after tumor transplantation.
Figure 6B:
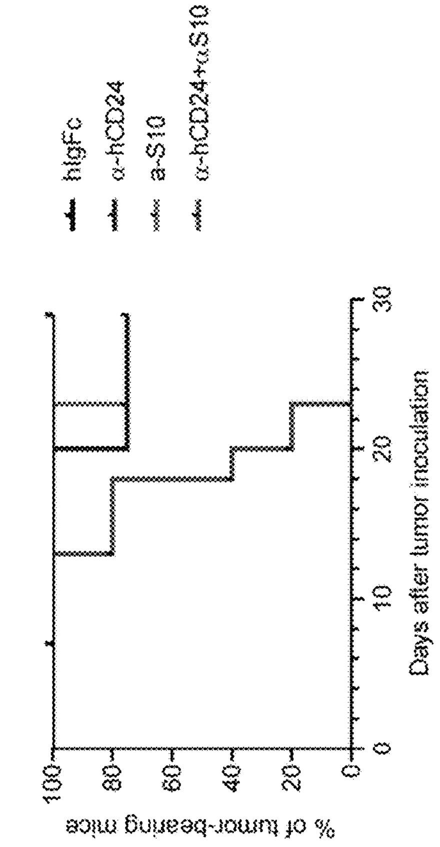

Since 31F11 promotes ADCC in vitro, we hypothesized that the antibody may promote tumor rejection when used in combination with a tumor-cell targeting antibody. To test this hypothesis, $1\times10^6$ MC38-hCD24 cell were inoculated on S10 BM Chimeric mice (n-4-5). Mice were treated with 100 μg hIgFc, α-hCD24, 31F11 (αS10) or α-hCD24+ 31F11 on day 7, 10, 13 and 16. As shown in FIG. 6, the combination of anti-CD24 and 31F11, but not either alone induced tumor rejection in all recipient mice. These data support the use of anti-Siglec-10 antibodies in tumor rejection.

Example 5

Humanization of 31F11 for Cancer Therapy

By blasting a human Ig database, human germline V region sequence IGHV2-70*04 and J region sequence JH6 were applied as the human framework acceptor for the CDR regions of 31F11 VH. Human germline V region IGKV3-15*01 and J region sequence JK4 were applied as the human framework acceptor for the CDR regions of 31F11 VL. 5 huVH versions (VHv1, VHv2, VHv3, VHv4, and VHv5, having SEQ ID NOS: 9-13) and 5 huVL versions (VLv1, VLv2, VLv3, VLv4, and VLv5, having SEQ ID NOS: 14-18) were designed.

To select the best working combination(s) of HuVH and HuVL for Siglec-10 binding, DNA encoding the heavy and light chains were synthesized in expression constructs and different combinations were co-transfected into 293 cells, 7 humanized antibodies and the chimeric parental antibody were compared for their binding to Jurkat cells expressing human Siglec-10. The properties of the clones are summarized in Table 2.

TABLE 2

Characterization humanized clones of 31F11

| | Yield (mg/ml) | Rk | Tm1 | Tm2 | | ADCC EC50 (ng/ml) | Rk | Binding EC50 (ng/ml) | Rk | ka (1/Ms) | Rk | kd (1/s) | Rk | KD (M) | Rk |
|---|---|---|---|---|---|---|---|---|---|---|---|---|---|---|---|
| Chimeric | 12.64 | | 65.8 | N/A | | 94.44 | | 210.8 | | 3.13E+05 | | 5.02E−04 | | 1.61E−09 | |
| 21# | 9.98 | 2 | 63.7 | 78.5 | 7 | 153.3 | 1 | 242.4 | 4 | 2.72E+05 | 2 | 5.89E−04 | 5 | 2.17E−09* | 4 |
| 22# | 14.83 | 1 | 63.8 | 78.5 | 6 | 265.7 | 5 | 237.1 | 2 | 1.64E+05 | 3 | 2.02E−04 | 2 | 1.23E−09 | 2 |
| 23# | 9.73 | 3 | 64.0 | 80.6 | 5 | 342.4 | 7 | 237.3 | 3 | 1.31E+05 | 4 | 1.97E−04 | 1 | 1.50E−09 | 3 |
| 32# | 6.62 | 5 | 66.9 | N/A | 2 | 182.6 | 3 | 422.7 | 7 | | | | | | |
| 34# | 2.99 | 7 | 64.4 | 71.7 | 4 | 273 | 6 | 365.3 | 6 | | | | | | |
| 52# | 5.56 | 6 | 66.6 | N/A | 3 | 157.2 | 2 | 228 | 1 | 4.41E+05 | 1 | 3.70E−04 | 4 | 8.40E−10 | 1 |
| 54# | 7.72 | 4 | 69.1 | N/A | 1 | 261.8 | 4 | 322.7 | 5 | 9.87E+04 | 5 | 2.15E−04 | 3 | 2.18E−09 | 5 |

Each column labeld "Rk" indicates the relative ranking of each parameter in the preceding column.
*This measurement used data from a separate experiment, so the relative ranking is less reliable.

Figure 7:
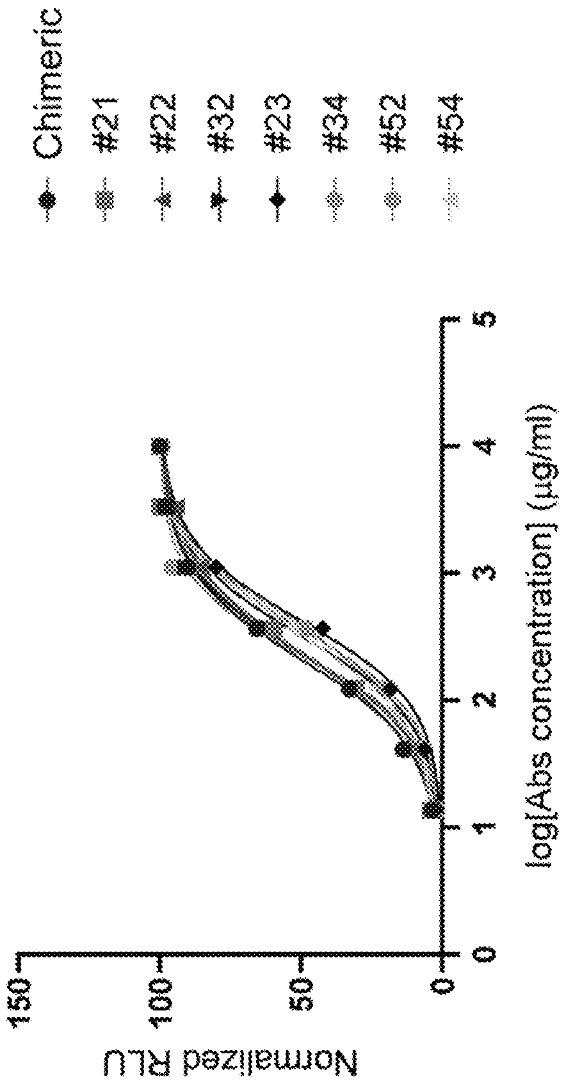
FIG. 7 shows characterization of humanized 31F11 clones for their binding to cell surface Siglec-10, ectopically expressed on Jurkat cells. Data shown are % of maximal binding over grading doses of antibodies.
Figure 8:
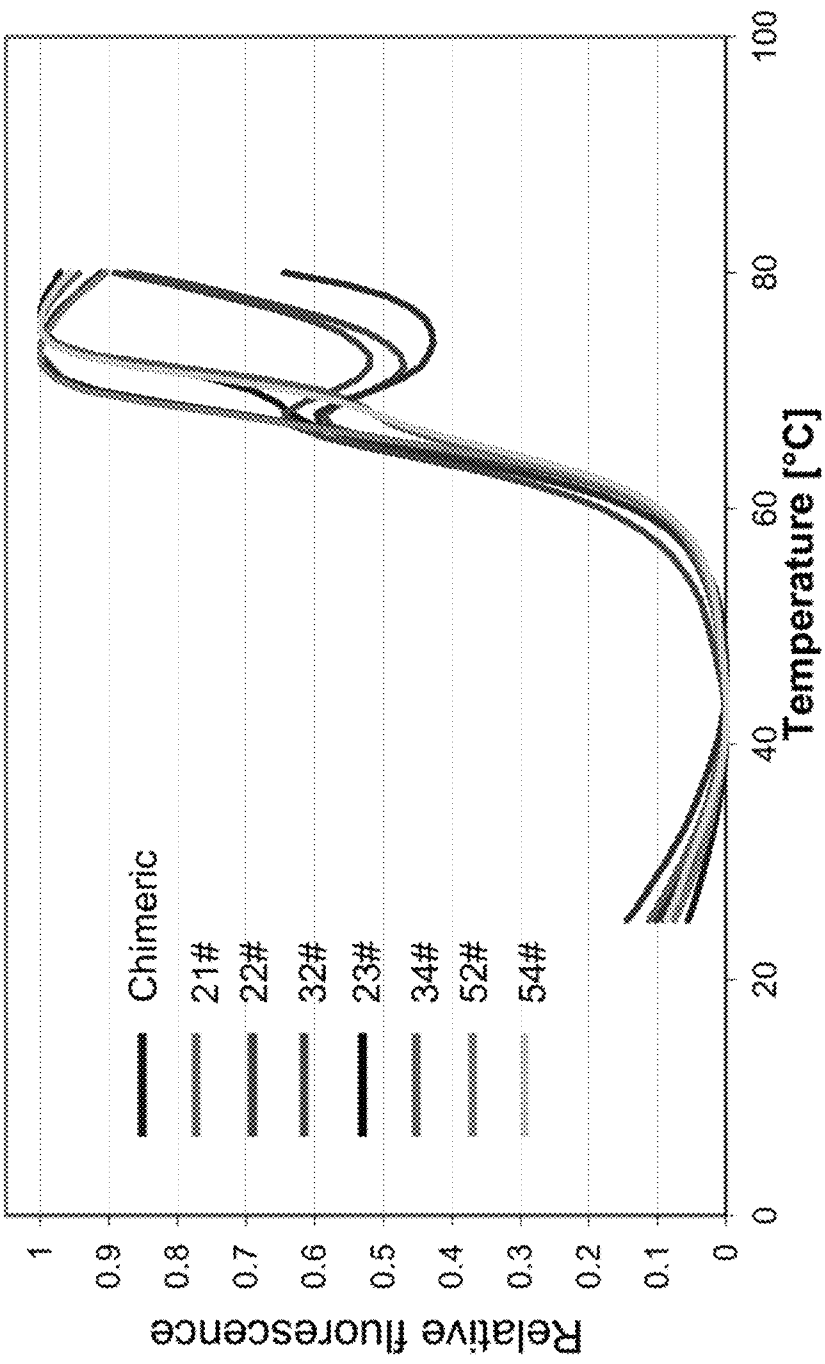
FIG. 8 shows thermal stability of humanized 31F11 clones. The data for each are shown in Table 1.

The antibody combinations are as follows: #21 (SEQ ID NOS: 9 and 15), #22 (SEQ ID NOS: 10 and 15), #23 (SEQ ID NOS: 11 and 15), #32 (SEQ ID NOS: 10 and 17), #34 (SEQ ID NOS: 12 and 17), #52 (SEQ ID NOS: 10 and 16), and #54 (SEQ ID NOS: 12 and 16). Among them, the parental antibody had an $EC_{50}$ of 210 ng/ml, while the humanized antibodies had an $EC_{50}$ between 228 ng/ml and 423 ng/ml (FIG. 7). This suggests that all antibodies showed potent binding to cell surface Siglec-10. Thermal stability analysis showed that all humanized antibodies exhibit good thermal stability (FIG. 8). Using Biacore analysis, we measured the affinity of the 5 top ranked antibodies. As shown in Table 2, all 5 antibodies tested show high affinity binding for Siglec-10. In particular, three of the five antibodies (#22, #23 and #52) had higher affinity than the chimeric parental clone.

To test the biological function, we compared the 7 mAbs with the parental chimeric antibodies for their ability to restore ADCC activity. As shown in FIG. 9, strong ADCC was detected among all clones tested.

Example 6

Pre-Clinical Studies of Anti-Siglec-10 Antibodies

Preclinical studies suggest that the therapeutic efficacy of anti-CTLA-4 mAbs is due to depletion of intra-tumoral Tregs, while their toxicity is due to down-regulation of CTLA-4. It is of interest to combine anti-CTLA-4 with a drug that can increase the ADCC of anti-CTLA-4. Siglec-10 has emerged as a promising target, as we have demonstrated that Siglec-10 is a negative regulator of ADCC, including ADCC triggered by anti-CTLA-4 (FIG. 10). anti-Siglec-10 mAb, 31F11 was developed based on its ability to enhance ADCC (FIG. 11) and phagocytosis of cancer cells (FIG. 12). The humanized version of the antibody is hereby developed for treatment of human cancer, named ONC-841.

Taken together, an antagonist of Siglec-10 may promote anti-tumor immunity by two distinct mechanisms. First, it may inactivate DNEMS to promote phagocytosis of tumor cells. Second, by inactivation of a negative regulator of ADCC, the antagonist may enhance the therapeutic activity of ADCC-based therapeutic antibodies.

Mechanism of Action

Accumulative data established that Siglec-10 is a negative regulator for phagocytosis, ADCC and ADCP. Therefore, ONC-841 can promote tumor rejection either as monotherapy or in combination therapy.

Monotherapy

As a monotherapy, ONC-841 promotes tumor rejection by blocking the Siglec-10-CD24 DNEMS interaction, as illustrated in FIG. 13. This mechanism should be most active for cancers that over-express CD24 or other high affinity Siglec-10 ligands. It is now clear that nearly 70% of all human cancer over-expresses CD24 and its expression corresponds to poor prognosis. In addition, Siglec-10 is also expressed at high levels in the tumor-associated macrophages (TAM). It is anticipated that ONC-841 can have broad impact in innate immunity against most cancer types, including non-small cell lung cancer.

Combination Therapy

Because Siglec-10 negatively regulates ADCC and ADCP, ONC-841 works synergistically with drugs that achieve anti-tumor activity by ADCC and ADCP. Such drugs may be targeting cancer cells (Erbitux, Rituximab, for example), or targeting host cells (anti-CTLA-4 antibodies, for example). Siglec-10 negatively regulates ADCC/ADCP and, while CD24 is capable of negatively signaling Siglec-10 to inhibit ADCC/ADCP, data demonstrate that Siglec-10 can recognize non-CD24 ligands. Therefore, ONC-841 can be used to enhance depletion of either host or cancer cells for tumor types independent of CD24 expression. FIG. 13 illustrates the mechanism by which ONC-841 can used in combination with an anti-CTLA-4, such as ONC-392, to promote depletion of Treg in the TME, namely by blocking negatively signaling by Siglec-10.

Example 7

Pharmacology and Toxicology of Anti-Siglec-10 Antibodies

In Vitro Pharmacology

Specificity of ONC-841

To confirm the binding specificity of ONC-841, we tested its binding to other human Siglec recombinant proteins by ELISA. Different Siglec extracellular domain recombinant proteins with either His or Fc tag were coated onto ELISA plates. Biotinylated ONC-841 was added to detect binding to the coated Siglec protein. Avidin-HRP was used as the secondary antibody for detection. As shown in FIGS. 14A and B, ONC-841 binds strongly to Siglec 10 with a Kd of ~0.02247 μg/mL, but not to all other Siglecs tested, including Siglecs 1-9, 11, 14 and 15. ONC-841 showed some binding to Siglec-5Fc, Siglec-6Fc, Siglec-11Fc and Siglec-14Fc at high concentration. To elucidate whether the binding was specific to Siglec recombinant proteins or nonspecific binding to Fc, we included human IgG1 Fc (hIgG1Fc) as a control. The result suggested that binding of ONC-841 to Siglec-5Fc, Siglec-6Fc, Siglec-11Fc and Siglec-14Fc is due to non-specific binding to the Fc tag as binding is comparable to hIgGFc. (FIG. 14B).

ONC-841 Blocks Siglec-10 Interaction with its Ligand on Human Malignant Jurkat Cells and In Vitro Differentiated Regulatory T Cells Siglec proteins recognize sialylated proteins on the surface of cells, with preference for α2,6 sialylation over α2,3-sialylation. To test whether ONC-841 blocks the interaction of Siglec-10 with its natural ligand on malignant cells, we tested the ability of ONC-841 to block Siglec-10Fc binding to the human leukemia Jurkat cell line. Siglec-10Fc-biotin was pre-complexed with streptavidin-PE (SA-PE) at a 4:1 molar ratio for 1 h and then added to different concentrations of ONC-841 for 5 min. The mix was added to Jurkat-CTLA4 cells at a concentration of 10 μg/mL based on Siglec-10Fc-biotin concentrations for an hour incubation at room temperature. Cells were thoroughly washed to remove excess of unbound reagents and acquired by flow cytometer. Analysis was done after exclusion of dead cells. As shown in FIG. 15, Siglec-10Fc binds strongly to the Jurkat cell line, and this binding is blocked by ONC-841 in a dose-dependent manner. The IC50 is estimated to be 2 μg/mL (13.3 nM).

To test the effect of ONC-841 on Siglec-10Fc-biotin binding to normal host cells, we used fluorescent Siglec-10Fc tetramers and evaluated the effect of ONC-841 using the same method mentioned above. We focused on Treg in order to support our proposed combination therapy. Treg were differentiated from naïve CD4 T cells isolated from fresh PBMC. As shown in FIG. 16, Siglec-10Fc show clear binding to in vitro differentiated human Treg. The interaction of Siglec-10Fc with Tregs was blocked in a dose-dependent manner by ONC-841. The IC50 is estimated to be 3.57 μg/mL (23.8 nM).

ONC-841 Promotes ADCC Reporter Activities of Both Cancer Targeting Antibodies

ONC-841 was tested for its ability to promote the ADCC activity of cancer targeting antibodies, including those that target CD20, CTLA-4, and epidermal growth factor receptor (EGFR). Utilizing Promega's ADCC reporter assay, we measured the ADCC activities by detecting luminescence expressed by NFAT in the effector cells upon activation of FcγRIIIA in the presence of cancer targeting antibodies. Briefly, target cells were co-incubated with either ADCC effector cells, mock transferred ADCC effector cells (ADCC-Mock), or human Siglec-10 expressing ADCC cells (ADCC-hSiglec10). Tumor-targeting antibody were added at a fixed concentration with titrated ONC-841 mAb. Relative luminescence units (RLU) was measured. As shown in FIG. 17A, ONC-841 promoted ADCC activity against the Raji lymphoma cell line by anti-CD20 with an EC50 of 0.5 μg/ml. To test the impact of ONC-841 on solid tumors, we used the B16 melanoma cell line expressing human EGFR and used the anti-EGFR drug, cetuximab, to trigger ADCC. As shown in FIG. 17B, ONC-892 nearly doubled the ADCC activity of cetuximab, with an EC50 of 0.3 μg/ml. To support our combination therapy trial design, we tested the efficacy of ONC-841 in promoting ADCC by ONC-392. As shown in FIG. 17C, ONC-841 enhanced the ADCC activity of ONC-392 with an IC50 of 0.08 μg/ml. The fact that the EC50 is the lowest for the combination with ONC-392 supports our selection of ONC-392 as the combination partner in early clinical trials, and the broad activity suggests the potential of using ONC-841 for combination therapy with cancer-targeting antibodies in both hematological malignancies and solid tumors.

ONC-841 Promotes ADCC and Antibody-Independent Killing of Leukemia Cells by Human NK Cells To test the impact of ONC-841 on tumor cell killing by NK cells, we used CTLA-4 transfected Jurkat cells as target cells and freshly isolated human NK cells as effector cells. Briefly, Calcein AM-labeled Jurkat-CTLA-4 target cells were co-incubated with negatively selected human NK cells from fresh whole blood with or without ONC-392 at fixed concentration with titrated ONC-841 mAb for 6 hour. After incubation, cells were analyzed by flow cytometry. Percent cell death was calculated based on number of remaining Calcein AM+ live cells in comparison to the control. As shown in FIGS. 18A-C, ONC-841 enhanced NK-mediated cell killing of Jurkat cells in the absence of tumor cell-targeting antibody, with an estimated EC50 of 0.3744 μg/ml. In the presence of saturating amounts of ONC-392 (20 μg/ml), ONC-841 further enhanced NK cell activity, with an estimated EC50 of 2.274 μg/ml. Therefore, ONC-841 promoted both ADCC and antibody independent cytolysis of malignant leukemia cells by NK cells.

ONC-841 Promotes Human Tumor Cell Killing by Human PBMC

Siglec-10 is expressed primarily on myeloid cells. Therefore, the impact of ONC-392 would likely extend beyond NK cells. To get a more comprehensive understanding of the anti-tumor effect, we tested the effect of ONC-841 on leukemia cell lysis by PBMC isolated from fresh whole blood of 3 individual donors. Calcein AM-labeled Jurkat-CTLA-4 target cells were co-incubated with PBMCs isolated from fresh whole blood with titrated ONC-841 mAb. After incubation, cells were analyzed by flow cytometry. Percent cell death was calculated based on number of remaining Calcein AM+ live cells in comparison to the control. As shown in FIG. 19, significant lysis was achieved with low doses of ONC-841, with the estimated EC50 of Donor 1, Donor 2, and Donor 3 at 0.3645, 0.01761, and 0.009572 μg/ml, respectively. These data demonstrate that ONC-841 can promote leukemia killing in the absence of leukemia targeting antibodies.

In Vivo Pharmacology Studies

To test the therapeutic activity ONC-841 in animal models, we generated a transgenic mouse model in which we removed mouse Siglec-G and inserted its human Siglec-10 ortholog by targeted mutation of the Siglecg gene and insertion of a Bacmid clone containing human Siglec-10, respectively (see below). Since the tissue distribution of Siglec-10 in the transgenic mice is consistent with its distribution in human leukocytes, we used this model to test impact of ONC-841 on tumor rejection, in two separate models.

Monotherapy and Combination Therapy with Cancer Targeting Antibody

To evaluate the therapeutic effect for solid tumors, we used a B16F10 cell line expressing human EGFR. At 6 days after tumor cell challenge, the tumor-bearing mice were treated with control IgG, ONC-841 or ONC-841+cetuximab, and measured tumor growth in a blinded fashion. B16-EGFR tumor-bearing (s.c.) Siglec10TG$^{+/+}$; Siglecg$^{-/-}$ mice (n=4-5) were treated i.p. with 200 μg of control hIgGFc or ONC-841 and i.t. with 10 μg of control hIgGFc or Cetuximab every three days for four injections, starting on day 6 after tumor inoculation. As shown in FIG. 20, intratumoral injection with cetuximab had minimal effect, while partial retardation of tumor growth was achieved with monotherapy with ONC-841. In combination, more significant retardation of tumor growth was achieved. These data suggest that ONC-841 has therapeutic activity for solid tumors in the mouse model.

To test the amounts of ONC-841 required for 50% reduction in tumor volume, we titrated the dose of ONC-841 in the combination therapy model. The dose of intratumoral treatment of cetuximab was fixed at 10 μg/injection, while that of systemic ONC-841 was 5, 10 and 20 mg/kg. Briefly, $5\times10^5$ B16-EGFR tumor cells were injected (s.c.) into Siglec10TG$^{+/+}$; Siglecg$^{-/-}$ mice (n=4-5) and treatment was initiated when the tumors reached 4-7 mm in diameter. The tumor bearing mice were treated i.p. with 2.5, 10 or 20 mg/kg ONC-841 and injected i.t. with 10 μg hIgFc or Cetuximab every three days for four injections. As shown in FIG. 21, a ONC-841 dose-dependent reduction of tumor volume was achieved. Using linear regression analysis, the EC50 of ONC-841 was determined to be 16.49 mg/kg.

Combination Therapy with Anti-CTLA-4 Antibody

As a model to show the combination effect of ONC-841 with host targeting immunotherapeutic antibodies, we used the unmodified B16F10 model and anti-mouse CTLA-4 mAb, 9D9. As shown in FIG. 22, neither 9D9 nor ONC-841 caused tumor growth retardation. However, in combination, significant reduction in tumor growth was observed.

Pharmacologically Relevant Species

ONC-841 does not React with Mouse and Non-Human Primate Siglec G/10

Siglec proteins are known to evolve rapidly with limited homology among orthologs from different species. Human Siglec-10 has high similarities to some of its NHP orthologs: 90% similarity to cynomolgus and rhesus Siglec-10 whereas the similarity to mouse Siglec-G is only 60% (from: Ensembl.org).

To determine which animal species are appropriate toxicology species for ONC-841 we evaluated ONC-841 antibody binding to NHP Siglec-10 or the mouse ortholog Siglec-G in 3 assays:

A. Binding to recombinant Siglec-10/Siglec-G

B. Binding to expi293 cells transiently expressing NHP Siglec-10/Siglec-G

C. Binding to cynomolgus PBMC

None of the assays showed specific binding of ONC-841 to NHP Siglec-10 or mouse Siglec-G, suggesting that the specific epitope to which ONC-841 binds is not shared with these species.

Binding to Recombinant Siglec-10/Siglec-G from Other Species

Recombinant His-tagged human and Cynomolgus Siglec-10 and mouse Siglec-G were purchased from ACROBiosystems. The Siglec proteins were coated on ELISA plate as capture antigen. Captured ONC-841 was detected using goat anti-human antibody. As shown below in FIG. 23, ONC-841 showed specific binding to human Siglec-10, but not to either cynomolgus or mouse proteins.

Binding to 293T Cells Transfected with NHP Siglec-10 Genes

The expi293 cells were transfected with human, cynomolgus, rhesus and marmoset Siglec-10 expression plasmids, respectively, to produce these proteins on the surface of cells. Binding of ONC-841 was evaluated using flow cytometry on live expi293 cells and expression of the different Siglec-10 proteins was validated using a polyclonal antibody to Siglec-10 (FIG. 24, lighter grey line). ONC-841 showed binding only to cells expressing human Siglec-10 but not to any of the NHP Siglec-10 (FIG. 24, darker grey line).

Binding to Cynomolgus PBMCs

To test binding of ONC-841 to natively expressed Siglec-10, human and cynomolgus PBMCs were stained and evaluated by flow cytometry. Siglec-10 is expressed by both monocytes (CD14$^+$ cells) and B cells (CD20$^+$ cells) and, therefore, ONC-841 binding was tested on these populations. To validate specific staining and eliminate possible binding of ONC-841 through the Fc receptor, an additional cell sample of each species was blocked with excess of human IgG before staining. ONC-841 clearly showed highly specific binding to both human monocytes and B cells, and the binding was unaffected by the presence of excess amount of human IgG (FIG. 25). In contrast, ONC-841 displayed weak binding to both cell sub-populations of cynomolgus. In addition, the excess amount of human IgG significantly reduced this binding, indicating low to non-specific binding property of ONC-841 to these NHP Siglec-10 (FIG. 27).

Generation of Human SIGLEC10 Transgenic Mice without Endogenous Siglecg Gene: Siglec10TG$^{+/+}$; Siglecg$^{-/-}$ Since ONC-841 does not bind leukocytes from available species of NHP and mouse, neither NHP nor mouse are considered relevant species for toxicity and pharmacological studies. Other commonly used toxicity species are genetically further distant from human than the NHPs tested, and thus less likely relevant for toxicity studies. Therefore, we set out to develop a transgenic mouse model for toxicity studies in which the human Siglec10 gene replaces its mouse ortholog, Siglecg.

The Siglec10 transgenic line (hereby called Siglec10TG$^{+/+}$) was created from C57/BL6 mice by Cyagen, Inc. (Santa Clara, CA) using a Bacmid clone with genomic sequence containing the human Siglec10, Siglec8 and Siglec12 genes. Use of the genomic clone with human regulatory and coding sequences may allow the mouse to express Siglec10 in a manner substantially similar to that in human leukocytes. Our data presented herein support this hypothesis. In addition, to capture the effect of blocking Siglec-10 in vivo, we removed the endogenous mouse Siglecg gene by crossing the transgene into the Siglecg$^{-/-}$ mouse in which Exons 2-11 of Siglecg were replaced by a GFP/Neo cassette.

The C57BL/6 Siglec10TG$^{+/+}$; Siglecg$^{-/-}$ line was created by crossing Siglec10TG$^{+/+}$ with Siglecg$^{-/-}$ mice. F1 and F2 generations of the cross-bred mice were screened for expression of both hSiglec-10 and Siglec-G by flow cytometry of blood cells (FIG. 26 top and middle) to select the desired genotype of Siglec10TG$^{+}$; Siglecg$^{-/-}$. This staining confirmed the expression of human Siglec-10 and lack of mouse Siglec-G. The data showed expression of Siglec-10 in >30% of mouse B cells, NK cells, monocytes, dendritic cells (DC) and neutrophils, and <10% of T cells in mouse PBMC.

To compare the binding of ONC-841 to subpopulations of cells in the blood observed in Siglec10TG$^{+/+}$; Siglecg$^{-/-}$ to ONC-841 binding to human cells expressing endogenous Siglec-10, human PBMCs were stained for lineage markers and either fluorescently labeled ONC-841 or commercially available anti-Siglec-10 antibody. FIG. 26 bottom panel showed clear staining of Siglec-10 by ONC-841 on monocytes, and B cells while T cells had no apparent staining as is reported in the literature. Surprisingly, no clear staining of NK cells in the blood, either CD16-positive or 16-negative NK cells although the data showed that ONC-841 enhanced ADCC activity of NK cells isolated from PBMC (FIG. 26). One possible explanation is that the human NK cells express lower amounts of Siglec-10 and the current assay is not sensitive. Another option is that the NK cells from human PBMCs were purchased frozen and were thawed for Siglec-10 staining. The discrepancy observed between Siglec10TG$^{+/+}$; Siglecg$^{-/-}$ will be further investigated.

Immunohistochemistry was performed on frozen sections from Siglec10TG$^{+/+}$; Siglecg$^{-/-}$ mice to detect ONC-841 binding in the mouse tissues. Briefly, flash-frozen mice tissues were sectioned and mounted on slides. The sections were blocked and then probed with 1 μg/mL of ONC-841, followed by detection using an anti-human secondary antibody labeled with HRP. Binding of ONC-841 was visualized using DAB as chromogen substrate for HRP, which gives a brown color, and the slides were counterstained with hematoxylin to visualize the cells nuclei in blue. Examination of the slides showed staining of immune cells in hematopoietic organs and most other tissues. This was a preliminary experiment which will be repeated, and sections will be examined by a trained pathologist. Examples of staining can be seen in FIG. 27.

The broad expression of Siglec-10 is seen on the tissue-resident leukocytes in most tissues/organs from Siglec10TG+/+; Siglecg−/− mice suggests that the mouse model will be valuable for toxicity and pharmacology studies.

In Vitro Cytokine Release Assays

Certain monoclonal antibody therapeutics have been shown to induce a range of acute infusion reactions including cytokine release syndrome (CRS) that can lead to adverse events in patients. On a molecular level, CRS is characterized by increased levels of TNF-α and IFN-γ 1-2 hours after administration, followed by increases in IL-6, IL-10, and sometimes IL-2 and IL-8. In order to test ONC-841 for possible induction of CRS alone or in combination with ONC-392, a preliminary cytokine release assay (CRA) was carried out. ONC-841 with or without ONC-392 at different concentrations up to 2 mg/mL were coated in a 96-well plate overnight. Commercial human IgG antibody (hIgG) was used as a negative control, and CD3_CD28 beads were used as a positive control. The next day the plates were washed and PBMCs from 4 different healthy donors were added to the wells. Cytokine release into the supernatant were tested 48 hours after the addition of PBMCs using BioLegend's LegendPlex Human Inflammation Panel 1 (cat #740809) and included IL-10, IFN-α2, IFN-γ, TNF-α, MCP-1 (CCL2), IL-6, IL-8 (CXCL8), IL-10, IL-12p70, IL-17A, IL-18, IL-23, and IL-33. The assay was done with PBMCs from 4 different donors and results are representative data from one of the donors (FIG. 29). ONC-841 with or without ONC-392 did not induce cytokines over the levels detected for uncoated wells. The only wells where cytokines were induced were the positive control of CD3/CD28 beads. Some cytokines were also induced in the wells containing commercially sourced IgG4. Overall, the data suggests that ONC-841 does not induce cytokine release from wPBMCs and will not induce CRS in patients.

Additional in vitro assays will be performed to assess whether ONC-841, with or without ONC-392 at similar concentrations, is capable of inducing cytokine release from normal, resting human PBMC. The cytokine release assays were performed following protocols that would have predicted the high risk of CRS for TGN1412. At least 10 donors will be tested. Experiments performed with ONC-392 alone have shown that it does not directly activate T cells.

Example 8

Clinical Trial for Anti-Siglec-10 Antibodies Indication

For Phase 1, patients with a histologically or cytologically confirmed diagnosis of solid tumors who have progressive locally advanced or metastatic disease after failure of or intolerance to established standard medical anti-cancer therapies, as per standard of care guidelines, such as NCCN guidelines, will be enrolled.

For Phase 2, non-small cell lung cancer patients who have failed immunotherapy will be chosen for an open-label study to test clinical efficacy using Simon's two stage design.

Summary of Rationale

As exemplified by the success of anti-PD(L)1 and anti-CTLA-4 antibodies in the clinic, antibodies that release suppression of T cells in the tumor microenvironment have had transformative impact on the care of cancer patients. The success highlights the power of targeting immune checkpoints of adaptive T cell immunity. Recent studies have suggested that targeting innate immune checkpoints that restrain the function of NK cells and macrophages may provide new approaches to improve cancer immunotherapy. Among these putative innate checkpoints are the pathways that negatively regulate phagocytosis or killing of tumor cells by macrophage and NK cells. Molecules that repress macrophage phagocytosis are collectively called "do-not-eat-me" signals (DNEMS). Among the known DNEMS, the CD47-SIRPα pathway is a prime innate immune checkpoint for cancer immunotherapy and anti-CD47 mAbs are being actively tested in clinical studies.

Preclinical studies have revealed the CD24-Siglec-10 interaction as a potent DNEMS that rivals CD47-SIRPα pathway. The CD24-Siglec-10 pathway was first revealed by OncoC4 co-founders as an innate immune checkpoint to minimize inflammatory response to tissue injuries [4]. CD24Fc, a Siglec-10 agonist, has been shown to exert protection against viral pneumonia and viral colitis. A recent Phase 3 clinical trial has demonstrated that CD24Fc confers significant protection against hospitalized COVID-19 patients. In contrast, despite strong preclinical data that targeting this pathway promotes tumor cell phagocytosis, an antagonist of CD24-Siglec-10 pathway has not been tested clinically. The proposed clinical trial may fill this major gap by testing the safety and efficacy of an anti-Siglec-10 mAb, ONC-841, in cancer patients who have failed or cannot tolerate standard of care therapeutics.

In addition to its role in promoting phagocytosis of tumor cells by macrophages, our preclinical studies revealed that ONC-841 also promoted antibody-dependent cell-mediated cytotoxicity (ADCC). This new finding prompts us to test ONC-841 in combination with drugs whose primary function is through antibody-dependent cell-mediated cytotoxicity (ADCC) and/or ADCP, including cancer-cell targeting and immune cell targeting antibodies. Cytotoxic T-lymphocyte-associated protein 4 (CTLA-4), also known as CD152 (cluster of differentiation 152), is a cell surface protein receptor that interacts with B7-1 (CD80) and B7-2 (CD86) to ensure proper function of regulatory T cells and protects host against autoinflammatory diseases. Anti-CTLA-4 monoclonal antibodies (mAbs) such as the approved antibody, Ipilimumab (marketed as YERVOY® by Bristol Myers Squibb), have demonstrated strong and broad cancer immunotherapeutic effects (CITE) in a variety of preclinical models and are used clinically both as monotherapy and as part of combination therapy with Nivolumab (anti-PD-1, marketed as OPDIVO® by Bristol Myers Squibb). However, CTLA-4 monotherapy has more immunotherapy-related adverse effects (irAEs) than anti-PD-1/PD-L1 therapy. In addition, the rate of severe irAE (Grades 3 and 4) reached 55% in melanoma patients receiving combination of Ipilimumab and Nivolumab. The severe irAEs further limit the doses tolerated by cancer patients. Nevertheless, Ipilimumab in combination with anti-PD-1 Nivolumab resulted in significantly improved response rates and overall survival in multiple types of cancer. Furthermore, anti-CTLA-4 antibodies induce long-lasting immunity in cancer patients. Therefore, CTLA-4 remains an important immunotherapy target, but major challenges remain in improving both safety and efficacy of anti-CTLA-4 mAbs.

ONC-392 is a highly selective, humanized monoclonal IgG1-kappa isotype antibody against CTLA-4. We have demonstrated that ONC-392 dissociates from CTLA-4 under low pH to allow its escape from lysosomal degradation and recycle to the cell surface. We have provided several lines of evidence for the notion that a pH-sensitive antibody like ONC-392 is not only safer but also more effective in Treg depletion and tumor rejection than Ipilimumab, which is pH-insensitive.

Since the therapeutic efficacy of anti-CTLA-4 mAbs is due to depletion of intra-tumoral Treg by ADCC and/or ADCP, while their toxicity is due to down-regulation of CTLA-4, it is of interest to combine ONC-392 with ONC-841 to see if this may lead to more potent anti-tumor activity through enhanced ADCC to deplete Treg, while at the same time maintaining ONC-392 in a safer dose level to avoid irAEs.

Siglec-10 has emerged as a promising target for immunotherapy. The preclinical studies from in vitro and in vivo studies have demonstrated that Siglec-10 is a negative regulator of ADCC, including ADCC triggered by ONC-392. We have developed ONC-841 based on its ability to enhance ADCC of ONC-392. We have demonstrated in an animal model that ONC-841 enhanced tumor-rejection induced by anti-CTLA-4 mAb.

Taken together, as an antagonist of Siglec-10, ONC-841 may promote anti-tumor immunity by two distinct mechanisms. First, it may inactivate a DNEMS to promote phagocytosis of tumor cells. Second, by blocking the negative signaling through Siglec-10 in ADCC, ONC-841 may enhance the therapeutic activity of ADCC-based therapeutic antibodies. To take full advantage of these biological activities and therapeutic potential, the current study is designed to evaluate the safety, pharmacokinetics and efficacy of ONC-841 as monotherapy and ONC-841 in combination with ONC-392 in patients with advanced or metastatic solid tumors.

Summary of Study Design

A Phase ½ open label dose-escalation study of intravenous (IV) administration of ONC-841 as a single agent and in combination with ONC-392 in participants with advanced/metastatic solid tumors.

Phase 1A, Dose Finding Studies

The Phase 1A study consists of two parts, to respectively define RP2D for monotherapy (Part A) and for combination therapy (Part B):

(1) Part A: A monotherapy dose escalation to define Recommended Phase 2 Dose for monotherapy (RP2D-M). The dose escalation of ONC-841 will enroll ONC-392 naïve patients with advanced cancer of various histology types. Six levels of ONC-841 will be tested with the starting dose to be determined pending on GLP toxicity data. ONC-841 will be administered by IV infusion, once every 21 days (q3w). The study will use intrapatient dose escalation until the second highest dose, at which point it will transition to a 3+3 design. Six patients will be enrolled at the final dose level with the option to de-escalate if a DLT is observed in 2 or more patients. The RP2D-M will be determined as the highest dose level where less than 2 in 6 patients developed a DLT.

(2) Part B: A combination therapy dose finding study to determine the Recommended Phase 2 Dose for ONC-841 in combination (RP2D-C) with 3.0, 6.0 or 10.0 mg/kg of ONC-392. The first dose will be at one dose level lower than the RP2D-M, in combination with ONC-392, q3w. Three patients will be enrolled in the first cohort following a 3+3 design. If no DLT is observed, the dose will be increased to the RP2D-M. It there is one DLT, another 3 patients will be enrolled. If no more than one patient among six has a DLT, ONC-841 in the next cohort will be either at an intermediate level between one level lower than RP2D-M and RP2D-M, or at RP2D-M, as determined by safety data. Six patients will be enrolled at final dose level. The RP2D-C will be determined as the highest dose level where less than 2 in 6 patients developed a DLT.

Phase 1B, Expansion Cohorts

Phase 1B consists of two arms of dose expansion to test the safety and clinical activity of ONC-841 monotherapy at RP2D-M (Arm A) or that of the combination of ONC-841 at RP2D-C with ONC-392 at 3.0, 6.0 or 10.0 mg/kg (Arm B).

We plan to enroll 30 patients per arm with advanced solid tumors or who have disease progression under standard of care (SOC) or are intolerant to SOC. The eligibility criteria will be the same as those of Phase 1A.

Phase 2

Phase 2 trial will follow a Simon two stage design. In stage 1, a total of 29 non-small cell lung cancer patients will be enrolled to determine the objective response rate. If more than 4 or more patients achieved an objective response, the trial will move to stage 2 to enroll sufficient patients (80 to 130) to achieve 80% power to reject the null hypothesis that response rate is less than 20%.

We have ranked 22 major cancer types for their potential responsiveness to combination therapy using ONC-392+ ONC-841. which in turn was based on their immunological landscape reconstructed with RNAseq and genomic data in the TCGA database. As shown in FIG. 28, we generated a landscape of immune tumor microenvironment from RNAseq and genomic data of 7279 independent cancer samples belonging to 22 cancer types from The Cancer Genomics Atlas (TCGA) database. Primarily from genomic and RNAseq data of pre-treatment clinical samples of melanoma patients who were later identified as responsers and nonresponders to an anti-CTLA-4 antibody Ipilimumab, we identified 5 ranking components of responsiveness to anti-CTLA-4, including CTLA-4 gene expression, ADCC potential, mutation burden, as well as gene enrichment and cellular composition that favor CTLA-4 responsiveness. The total ranking number was calculated by the sum of 5 independent partitioning values, each comprised of 1-3 components. The ranking of response to ONC-841 is based on the abundance of SIGLEC10 expression and that of macrophages, established by RNAseq data. The ranking for response to combination therapy is based on that of their response to each of the antibodies (Table 3). Our analysis suggest that non-small cell lung adenocarcinoma is the most responsive cancer type. Single agent activity of ONC-392 is supported by our ongoing clinical trial.

TABLE 3

Relative ranking of 22 cancer types for their response to ONC-392, ONC-841 and their combination

| Cancer type | ONC-392 index | ONC-841 Index | Combination Rank Index |
|---|---|---|---|
| LUAD | 2 | 1 | 1 |
| SKCM-TM | 1 | 4 | 2 |
| LUSC | 5 | 3 | 3 |
| BRCA-Basal | 4 | 6 | 4 |
| BRCA-Her2 | 7 | 7 | 5 |
| PAAD | 8 | 8 | 6 |
| HNSC | 3 | 16 | 7 |
| KIRC | 9 | 10 | 8 |
| STAD | 6 | 14 | 9 |
| GBM | 21 | 2 | 10 |
| BRCA_LumB | 13 | 11 | 11 |
| BRCA_LumA | 14 | 13 | 12 |
| COAD | 10 | 17 | 13 |
| LGG | 22 | 5 | 14 |
| SKCM-TP | 12 | 15 | 15 |
| KIRP | 20 | 9 | 16 |
| OV | 18 | 12 | 17 |
| READ | 11 | 21 | 18 |
| LIHC | 15 | 19 | 19 |
| ESCA | 17 | 18 | 20 |
| BLCA | 16 | 20 | 21 |
| PRAD | 19 | 22 | 22 |

Based on our clinical data and in silico analysis, we have selected non-small cell lung adenocarcinoma as our first clinical indication in a Phase 2 study to test the clinical efficacy of combination therapy with ONC-841 and ONC-392.

Dosage/Dosage Form, Route, and Dose Regimen

For dose escalation in monotherapy, ONC-841 will be administered as a minimal 60 minute IV infusion. Six dose levels of ONC-841 will be evaluated. The dosing interval will be 21 days. ONC-841 will be given at the schedule of Q3W. In the combination of ONC-392 and ONC-841, ONC-841 will be administered first as a minimum of 60 min IV infusion. ONC-392 will then be administered as a minimum 60 minutes IV infusion at a 3.0, 6.0 or 10.0 mg/kg. ONC-392 and ONC-841 should not be mixed in administration and there should be an interval of at least 30 min between administration of the two drugs. ONC-841 alone or ONC-392 and ONC-841 combination will be given at the schedule of Q3W.

The invention claimed is:

1. An anti-Siglec-10 antibody, wherein the antibody comprises (a) a heavy chain variable region comprising a complementarity determining region (CDR) 1 comprising the sequence set forth in SEQ ID NO: 3, a CDR2 comprising the sequence set forth in SEQ ID NO: 4, and a CDR3 comprising the sequence set forth in SEQ ID NO: 5; and, (b) a light chain variable region comprising a CDR1 comprising the sequence set forth in SEQ ID NO: 6, a CDR2 comprising the sequence set forth in SEQ ID NO: 7, and a CDR3 comprising the sequence set forth in SEQ ID NO: 8.

2. The anti-Siglec-10 antibody of claim 1, wherein the antibody is a chimeric antibody.

3. The anti-Siglec-10 antibody of claim 1, wherein the heavy chain variable region comprises the sequence set forth in one of SEQ ID NOS: 9-13, and the light chain variable region comprises the sequence set forth in one of SEQ ID NOS: 14-18.

4. The anti-Siglec-10 antibody of claim 3, wherein the heavy chain variable region comprises the sequence set forth in SEQ ID NO: 9, 10, or 11, and the light chain variable region comprises the sequence set forth in SEQ ID NO: 15.

5. The anti-Siglec-10 antibody of claim 4, wherein the heavy chain variable region comprises the sequence set forth in SEQ ID NO: 9.

6. The anti-Siglec-10 antibody of claim 5, wherein the heavy chain comprises the sequence set forth in SEQ ID NO: 25.

7. The anti-Siglec-10 antibody of claim 6, wherein the light chain comprises the sequence set forth in SEQ ID NO: 27.

8. The anti-Siglec-10 antibody of claim 4, wherein the heavy chain variable region comprises the sequence set forth in SEQ ID NO: 10.

9. The anti-Siglec-10 antibody of claim 8, wherein the heavy chain comprises the sequence set forth in SEQ ID NO: 32.

10. The anti-Siglec-10 antibody of claim 9, wherein the light chain comprises the sequence set forth in SEQ ID NO: 27.

11. The anti-Siglec-10 antibody of claim 4, wherein the heavy chain variable region comprises the sequence set forth in SEQ ID NO: 11.

12. The anti-Siglec-10 antibody of claim 3, wherein the heavy chain variable region comprises the sequence set forth in SEQ ID NO: 10 or 12, and the light chain variable region comprises the sequence set forth in SEQ ID NO: 17.

13. The anti-Siglec-10 antibody of claim 12, wherein the heavy chain variable region comprises the sequence set forth in SEQ NO: 10.

14. The anti-Siglec-10 antibody of claim 12, wherein the heavy chain variable region comprises the sequence set forth in SEQ NO: 12.

15. The anti-Siglec-10 antibody of claim 3, wherein the heavy chain variable region comprises the sequence set forth in SEQ ID NO: 10 or 12, and the light chain variable region comprises the sequence set forth in SEQ ID NO: 16.

16. The anti-Siglec-10 antibody of claim 15, wherein the heavy chain variable region comprises the sequence set forth in SEQ ID NO: 10.

17. The anti-Siglec-10 antibody of claim 16, wherein the heavy chain comprises the sequence set forth in SEQ ID NO: 32.

18. The anti-Siglec-10 antibody of claim 17, wherein the light chain comprises the sequence set forth in SEQ ID NO: 34.

19. The anti-Siglec-10 antibody of claim 15, wherein the heavy chain variable region comprises the sequence set forth in SEQ ID NO: 12.

20. A method of treating a cancer in a patient in need thereof, comprising administering the anti-Siglec-10 antibody of claim 1 to the patient.

21. The method of claim 20, wherein the anti-Siglec-10 antibody is administered in combination with a second cancer therapy.

22. The method of claim 21, wherein the second cancer therapy is a cancer-targeting immunotherapy or an immune-cell-targeting immunotherapy.

23. The method of claim 22, wherein the second cancer therapy is an anti-CTLA-4 antibody.

24. The method of claim 20, wherein the cancer is an advanced solid tumor, a hematologic cancer, or a cancer that includes infiltrating cells that bind to the anti-Siglec-10 antibody.

25. The method of claim 24, wherein the cancer is an advanced solid tumor selected from the group consisting of lung adenocarcinoma (LUAD), a metastatic skin cutaneous melanoma (SKCM-TM), a lung squamous cell carcinoma (LUSC), a basal-like breast invasive carcinoma, a pancreatic adenocarcinoma, a head and neck squamous cell carcinoma, a kidney renal clear cell carcinoma, a stomach adenocarcinoma, a Luminal B breast invasive carcinoma, a Luminal A breast invasive carcinoma, a non-small cell lung cancer, a glioblastoma, a melanoma, a low grade glioma, a kidney cancer, a breast cancer basal type, a $Her2^{+}$ breast cancer, a pancreatic cancer, and an ovarian cancer.

26. The method of claim 25, wherein the lung adenocarcinoma is a non-small cell lung adenocarcinoma.

27. The method of claim 24, wherein the cancer is a hematologic cancer selected from the group consisting of a leukemia, a myeloid dysplasia syndrome, a B cell lymphoma, and a multiple myeloma.

28. The method of claim 25, wherein the $Her2^{+}$ breast cancer is a breast invasive carcinoma.

* * * * *